United States Patent
Hiroi et al.

(10) Patent No.: US 12,291,701 B2
(45) Date of Patent: May 6, 2025

(54) CELL CULTURE CONTAINER HAVING MINUTE VOLUME

(71) Applicant: NISSAN CHEMICAL CORPORATION, Tokyo (JP)

(72) Inventors: Yoshiomi Hiroi, Funabashi (JP); Kohei Suzuki, Funabashi (JP); Natsuki Abe, Shiraoka (JP)

(73) Assignee: NISSAN CHEMICAL CORPORATION, Tokyo (JP)

( * ) Notice: Subject to any disclaimer, the term of this patent is extended or adjusted under 35 U.S.C. 154(b) by 0 days.

(21) Appl. No.: 16/650,907

(22) PCT Filed: Sep. 26, 2018

(86) PCT No.: PCT/JP2018/035641
§ 371 (c)(1),
(2) Date: Mar. 26, 2020

(87) PCT Pub. No.: WO2019/065714
PCT Pub. Date: Apr. 4, 2019

(65) Prior Publication Data
US 2020/0291339 A1    Sep. 17, 2020

(30) Foreign Application Priority Data
Sep. 26, 2017 (JP) .................................. 2017-185397

(51) Int. Cl.
*C12M 1/00* (2006.01)
*C09D 185/02* (2006.01)

(52) U.S. Cl.
CPC ........... *C12M 23/20* (2013.01); *C09D 185/02* (2013.01); *C12M 23/22* (2013.01)

(58) Field of Classification Search
CPC ...... C12M 23/20; C12M 23/22; C09D 185/02
(Continued)

(56) References Cited

U.S. PATENT DOCUMENTS 5,178,963 A    1/1993 Faust et al.
5,643,561 A    7/1997 Katsuen et al.
(Continued)

FOREIGN PATENT DOCUMENTS

CA    2914616 A1    12/2014
CA    2970451 A1 *  6/2016    ............. A61L 27/34
(Continued)

OTHER PUBLICATIONS

Japanese Patent Office, International Search Report in International Patent Application No. PCT/JP2018/035641 (Dec. 18, 2018).
(Continued)

*Primary Examiner* — Michael L Hobbs
*Assistant Examiner* — Lenora A Abel
(74) *Attorney, Agent, or Firm* — Leydig, Voit & Mayer, Ltd.

(57) ABSTRACT

The invention relates to a cell culture container that inhibits adhesion of cells, a method for manufacturing the same and a method for producing cell aggregates using the same. The cell culture container has a coating film containing a copolymer having a recurring unit which contains a group represented by formula (a) and a recurring unit which contains a group represented by formula (b):

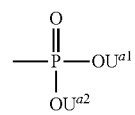

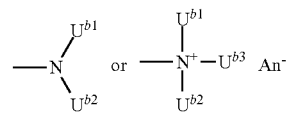

wherein $U^{a1}$, $U^{a2}$, $U^{b1}$, $U^{b2}$ and $U^{b3}$ each independently represent a hydrogen atom or a linear or branched alkyl group having 1 to 5 carbon atoms, and $An^-$ represents an anion selected from the group consisting of a halide ion, an
(Continued)

inorganic acid ion, a hydroxide ion and an isothiocyanate ion, on at least a part of a surface of the container, and the volume of the container is 20 µL or less.

19 Claims, 8 Drawing Sheets

(58) Field of Classification Search
USPC .................................................. 435/289.1
See application file for complete search history.

(56) References Cited

U.S. PATENT DOCUMENTS

| | | | |
|---|---|---|---|
| 5,648,442 | A | 7/1997 | Bowers et al. |
| 6,579,620 | B2 * | 6/2003 | Mizuno ................ C09D 127/18 524/588 |
| 10,774,165 | B2 | 9/2020 | Hyuugaji |
| 10,774,234 | B2 | 9/2020 | Otani et al. |
| 10,889,791 | B2 | 1/2021 | Katayama et al. |
| 11,470,841 | B2 | 10/2022 | Hiroi et al. |
| 2008/0045686 | A1 | 2/2008 | Meagher et al. |
| 2008/0063572 | A1 | 3/2008 | Deutsch et al. |
| 2008/0081369 | A1 | 4/2008 | Adkisson et al. |
| 2010/0028286 | A1 | 2/2010 | Carballada et al. |
| 2010/0096327 | A1 | 4/2010 | Gin et al. |
| 2012/0214230 | A1 | 8/2012 | Anneren et al. |
| 2014/0147879 | A1 | 5/2014 | Wakamoto et al. |
| 2014/0186945 | A1 | 7/2014 | Bradley et al. |
| 2015/0017221 | A1 | 1/2015 | Hayashi et al. |
| 2016/0032238 | A1 * | 2/2016 | Lawin .................... C12M 23/02 264/129 |
| 2016/0115435 | A1 * | 4/2016 | Otani .................... C08F 230/02 427/353 |
| 2016/0122576 | A1 | 5/2016 | Hiroi et al. |
| 2016/0129176 | A1 | 5/2016 | Kanaki et al. |
| 2016/0168294 | A1 | 6/2016 | Hayashi et al. |
| 2017/0101497 | A1 | 4/2017 | Koguchi et al. |
| 2017/0107470 | A1 | 4/2017 | Fang-Yen |
| 2017/0267960 | A1 | 9/2017 | Tsukada et al. |
| 2017/0335266 | A1 | 11/2017 | Noda et al. |
| 2017/0349777 | A1 | 12/2017 | Hiroi et al. |
| 2018/0223024 | A1 | 8/2018 | Hyuugaji |
| 2018/0305652 | A1 | 10/2018 | Katayama et al. |
| 2019/0218413 | A1 | 7/2019 | Hiroi et al. |
| 2019/0233792 | A1 | 8/2019 | Hiroi et al. |
| 2019/0327959 | A1 | 10/2019 | Hiroi et al. |
| 2020/0369999 | A1 | 11/2020 | Suzuki et al. |
| 2021/0171890 | A1 | 6/2021 | Nakajima et al. |
| 2022/0026440 | A1 | 1/2022 | Otsuka et al. |

FOREIGN PATENT DOCUMENTS

| | | | |
|---|---|---|---|
| CN | 105307698 | A | 2/2016 |
| EP | 1152242 | A | 11/2001 |
| EP | 2878664 | A1 | 6/2015 |
| EP | 3098299 | A1 | 11/2016 |
| EP | 3318585 | A1 | 5/2018 |
| EP | 3467095 | A1 | 4/2019 |
| GB | 1110042.7 | | 6/2011 |
| JP | H04-117276 | A | 4/1992 |
| JP | H05-156204 | A | 6/1993 |
| JP | H05-292957 | A | 11/1993 |
| JP | H08-140673 | A | 6/1996 |
| JP | H11-166015 | A | 6/1999 |
| JP | 2002-005887 | A | 1/2002 |
| JP | 2003-040937 | A | 2/2003 |
| JP | 2006-084393 | A | 3/2006 |
| JP | 2006-158961 | A | 6/2006 |
| JP | 2007-063459 | A | 3/2007 |
| JP | 2007-124982 | A | 5/2007 |
| JP | 2007-326920 | A | 12/2007 |
| JP | 2008-061609 | A | 3/2008 |
| JP | 2008-191067 | A | 8/2008 |
| JP | 2009-031121 | A | 2/2009 |
| JP | 2010-236955 | A | 10/2010 |
| JP | 2011-078316 | A | 4/2011 |
| JP | 2012-512637 | A | 6/2012 |
| JP | 2014-502610 | A | 2/2014 |
| JP | 2014-120410 | A | 6/2014 |
| JP | 2014-155471 | A | 8/2014 |
| JP | 2015-226497 | A | 12/2015 |
| JP | 2016-059690 | A | 4/2016 |
| JP | 2017-060498 | A | 3/2017 |
| JP | 2018-169349 | A | 11/2018 |
| NL | 7603497 | A | 10/1977 |
| WO | WO 2000/039582 | A1 | 7/2000 |
| WO | WO 2010/079058 | A2 | 7/2010 |
| WO | WO 2011/049524 | A1 | 4/2011 |
| WO | WO 2011/098365 | A1 | 8/2011 |
| WO | WO 2012/089337 | A1 | 7/2012 |
| WO | WO 2012/172291 | A1 | 12/2012 |
| WO | WO 2013/099901 | A1 | 7/2013 |
| WO | WO 2013/144372 | A1 | 10/2013 |
| WO | WO 2014/017513 | A1 | 1/2014 |
| WO | WO 2014/196650 | A1 | 12/2014 |
| WO | WO 2014/196652 | A1 | 12/2014 |
| WO | WO 2015/178413 | A1 | 11/2015 |
| WO | WO 2016/072369 | A1 | 5/2016 |
| WO | WO 2016/093293 | A1 | 6/2016 |
| WO | WO 2017/006850 | A1 | 1/2017 |
| WO | WO 2017/022815 | A1 | 2/2017 |
| WO | WO 2017/065279 | A1 | 4/2017 |
| WO | WO 2017/204201 | A1 | 11/2017 |
| WO | WO 2017/217336 | A1 | 12/2017 |
| WO | WO 2018/016463 | A1 | 1/2018 |
| WO | WO 2019/093442 | A1 | 5/2019 |
| WO | WO 2019/107503 | A1 | 6/2019 |
| WO | 2019/176515 | A1 | 9/2019 |
| WO | WO 2020/100957 | A1 | 5/2020 |

OTHER PUBLICATIONS

Liaw et al., "Polymerization and application of 2-methacryloyloxyethyl phenyl phosphate in coatings," *Die Angewandte Makromolekulare Chemie*, 214(3750): 169-178 (1994).
European Patent Office, Extended European Search Report in European Patent Application No. 18861999.3 (Oct. 15, 2020).
Dictionary.com, "Varnish," Dictionary Entry (2020).
Todaro et al., "Colon Cancer Stem Cells Dictate Tumor Growth and Resist Cell Death by Production of Interleukin-4," *Cell Stem Cell*, 1(4): 389-402 (2007).
China National Intellectual Property Office, The First Office Action in Chinese Patent Application No. 201680059049.1 (Dec. 27, 2019).
European Patent Office, Supplementary European Search Report in European Patent Application No. 16855532.4 (Sep. 28, 2018).
European Patent Office, Communication Pursuant to Article 94(3) EPC in European Patent Application No. 14808411.4 (Mar. 22, 2018).
European Patent Office, Communication Pursuant to Article 94(3) EPC in European Patent Application No. 16855532.4 (Oct. 11, 2018).
European Patent Office, Supplementary European Search Report in European Patent Application No. 17813233.8 (Apr. 9, 2019).
European Patent Office, Communication Pursuant to Article 94(3) EPC in European Patent Application No. 17813233.8 (Apr. 24, 2019).
European Patent Office, Extended European Search Report in European Patent Application No. 18876536.6 (Dec. 11, 2020).
Japanese Patent Office, International Search Report in International Patent Application No. PCT/JP2014/065250 (Aug. 19, 2014).
Japanese Patent Office, International Search Report in International Patent Application No. PCT/JP2016/080547 (Nov. 22, 2016).
Japanese Patent Office, International Search Report in International Patent Application No. PCT/JP2017/019147 (Aug. 15, 2017).
Japanese Patent Office, International Search Report in International Patent Application No. PCT/JP2017/021508 (Sep. 12, 2017).
Japanese Patent Office, International Search Report in International Patent Application No. PCT/JP2018/041556 (Jan. 29, 2019).

(56) References Cited

OTHER PUBLICATIONS

Japanese Patent Office, International Search Report in International Patent Application No. PCT/JP2018/044014 (Feb. 26, 2019).
Japanese Patent Office, International Search Report in International Patent Application No. PCT/JP2019/044605 (Feb. 10, 2020).
Japanese Patent Office, Notification of Reasons for Refusal in Japanese Patent Application No. 2015-521514 (Mar. 13, 2018).
European Patent Office, European Search Report in European Patent Application 19883598.5 (Jun. 2, 2022).
European Patent Office, Communication Pursuant to Article 94(3) EPC in European Patent Application 19883598.5 (Jun. 14, 2022).
Allen et al., "Surface-induced Changes in Protein Adsorption and Implications for Cellular Phenotypic Responses to Surface Interaction," *Biomaterials.*, 27(16): 3096-3108 (2006).
BD Biosciences, Product Information: "Corning Falcon 96-Well Cell Culture Plates, 351172 Plates with Untreated Surface, Sterile" [accessed Sep. 20, 2023].
U.S. Appl. No. 14/896,639, filed Dec. 7, 2015.
U.S. Appl. No. 15/768,427, filed Apr. 13, 2018.
U.S. Appl. No. 16/305,002, filed Mar. 28, 2019.
U.S. Appl. No. 16/310,325, filed Mar. 28, 2019.
U.S. Appl. No. 16/762,694, filed May 8, 2020.
U.S. Appl. No. 16/767,527, filed May 27, 2020.
U.S. Appl. No. 17/293,996, filed May 14, 2021.

\* cited by examiner

CELL CULTURE CONTAINER HAVING MINUTE VOLUME

CROSS-REFERENCE TO RELATED APPLICATIONS

This patent application is the U.S. national phase of International Patent Application No. PCT/JP2018/035641, filed on Sep. 26, 2018, which claims the benefit of Japanese Patent Application No. 2017-185397, filed on Sep. 26, 2017, which are incorporated by reference in their entireties herein.

TECHNICAL FIELD

The present invention relates to a cell culture container, a method for manufacturing the same and a manufacturing method of cell aggregates (which is also called to as sphere) using the same. In particular, the present invention relates to a cell culture container characterized in that a copolymer having a function of inhibiting adhesion of cells has been coated on the surface thereof, and a method for manufacturing the same.

BACKGROUND ART

In recent years, technologies to proliferate or maintain various organs, tissues and cells that play different roles in animals and plants in vitro have been developed. To proliferate or maintain these organs and tissues in vitro is called organ culture and tissue culture, respectively, and to proliferate, differentiate or maintain cells isolated from organs and tissues in vitro is called cell culture. The cell culture is a technology for proliferating, differentiating or maintaining isolated cells in a medium in vitro, and is indispensable for analyzing functions and structures of various organs, tissues and cells in vivo in detail. In addition, the cells and/or tissues cultured by the technology are utilized in various fields such as medical efficacy and toxicity evaluation of chemical substances, pharmaceuticals, etc., mass production of useful substances such as enzymes, cell growth factors, antibodies, etc., regenerative medicine to supplement organs, tissues and cells lost by diseases or damages, selective breeding of plants, creation of genetically recombined crops, and the like.

Cells derived from animals are roughly classified into two of floating cells and adherent cells due to their properties. Animal-derived cells are roughly classified into two of floating cells and adherent cells due to their properties. The floating cells are cells that do not require a scaffold for growth and proliferation, and the adherent cells are cells that require a scaffold for growth and proliferation, but most of cells constituting a living body are the latter adherent cells. As the culture methods of the adherent cells, monolayer culture, dispersion culture, embedding culture, microcarrier culture, and cell aggregates (sphere) culture, etc., have been known.

In particular, in recent years, accompanied with development of the regenerative medical field, sphere culture has attracted attention as a culture method in an environment closer to in vivo, and various medium compositions and medium additives suitable for the culture have been reported (for example, see Patent Documents 1 and 2). In addition, in the sphere culture, stimulation from the culture container (substrate) is considered to be an important factor affecting the results of the culture, and cells (in particular, cell aggregates) are required to culture in a three-dimensional environment or in a completely floating state without any stimulation from the culture container (for example, see Patent Document 3).

The present inventors paid attention to a polymer having a phosphate ester group, which is expected as a coating material having a function of inhibiting adhesion of various biological substances, and carried out in-depth studies. As a result, they have reported that a cell culture container at least a part of the surface of which is coated with a copolymer having a specific anionic group and cationic group can suppress adhesion of the cells to the container surface (inner surface) and the coating can be firmly adhered to the container surface, so that it is useful as a cell culture container improved in elution of the coating into the culture medium and radiation resistance (for example, see Patent Document 4).

PRIOR ART DOCUMENTS

Patent Documents

Patent Document 1: WO 2014/017513
Patent Document 2: WO 2013/144372
Patent Document 3: JP 2008-61609A
Patent Document 4: WO 2014/0196652

SUMMARY OF THE INVENTION

Problems to be Solved by the Invention

Heretofore, in order to culture cells (in particular, cell aggregates) in a three-dimensional environment or in a completely floating state, there were problems of adhesion of cells to the container surface and elution of the coating attached to the cell culture container into the culture medium. In addition, there was a problem of adhesion of proteins produced or secreted by cell culture or contained in the medium to the container surface. A cell culture container to which a coating of a hydrophilic compound has been attached can improve adhesion of cells to the container surface, but there were still problems of elution of the coating attached to the cell culture container and adhesion of the proteins to the container surface, etc.

Further, when the cell culture container is a material having a minute space (such as a cell culture dish having a large number of cavities, etc.), in a general coating agent having a function of inhibiting adhesion of biological substances, there was a problem of the so-called bubble biting in which bubbles remained in a film when the film was formed by coating, etc. This caused an adverse effect on stabilization of qualities (cell adhesion, protein adhesion, optical measurement, etc.) of the cell culture container.

Accordingly, an object of the present invention is to provide a cell culture container, a method for manufacturing the same and a method for manufacturing cell aggregates using the same. In particular, an object of the present invention is to provide a cell culture container character-in that a copolymer having a function of inhibiting adhesion of cells is coated with a uniform film thickness without any defects such as bubble biting, etc., on the surface thereof, a method for manufacturing the same and a method for manufacturing cell aggregates using the same.

Means to Solve the Problems

The present inventors have intensively studied so far to solve the above-mentioned problems, and as a result, they have found that a cell culture container in which a part of the surface of which has been coated by a copolymer having a specific hydrophobic group in addition to a specific anionic group and cationic group can inhibit adhesion of proteins to the container surface in addition to cells, the coating is firmly adhered to the container surface, and even more, when it is a cell culture container having minute spaces, a cell culture container onto which a coating having uniform film thickness without any defects such as bubble biting, etc., on the surface thereof, and without any defects such as flaw, etc., is formed can be manufactured, whereby the present invention has been completed.

That is, the present invention is as follows:

[1] A cell culture container which comprises having at least one opened minute space with a volume of 20 µL or less at a surface of the container, and provided with a coating film containing a copolymer having a recurring unit which contains a group represented by the following formula (a) and a recurring unit which contains a group represented by the following formula (b):

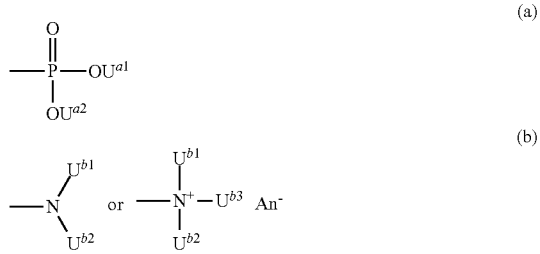

(wherein
$U^{a1}$, $U^{a2}$, $U^{b1}$, $U^{b2}$ and $U^{b3}$ each independently represent a hydrogen atom or a linear or branched alkyl group having 1 to 5 carbon atoms, and An$^-$ represents an anion selected from the group consisting of a halide ion, an inorganic acid ion, a hydroxide ion and an isothiocyanate ion) onto at least a part of the surface portion of the container constituting the minute space.

[2] The cell culture container described in [1], wherein the copolymer further has a recurring unit which contains a group represented by the following formula (c):

—R$^c$ (c)

[wherein
R$^c$ represents a linear or branched alkyl group having 1 to 18 carbon atoms, a cyclic hydrocarbon group having 3 to 10 carbon atoms, an aryl group having 6 to 10 carbon atoms, an aralkyl group having 7 to 15 carbon atoms or an aryloxyalkyl group having 7 to 15 carbon atoms (here, the above-mentioned aryl portion may be substituted by a linear or branched alkyl group having 1 to 5 carbon atoms which may be substituted by a halogen atom(s))].

[3] The cell culture container described in [1] or [2], wherein a difference between the maximum film thickness and the minimum film thickness of the coating film is 1,000 Å or less.

[4] The cell culture container described in any one of [1] to [3], wherein it is for manufacturing cell aggregates.

[5] The cell culture container described in any one of [1] to [4], wherein a water contact angle of a surface of the above-mentioned coating film is 0 to 120°, or a bubble contact angle in water is 80 to 180°.

[6] A method for manufacturing a cell culture container which comprises a step of bringing a coating agent into contact with a surface of a cell culture container having at least one opened minute space which has a volume of 20 µL or less, to form a coating film having a difference between the maximum film thickness and the minimum film thickness of 1,000 Å or less onto at least a part of the surface portion of the container constituting the minute space,
wherein the coating agent contains a copolymer having a recurring unit which contains a group represented by the following formula (a) and a recurring unit which contains a group represented by the following formula (b):

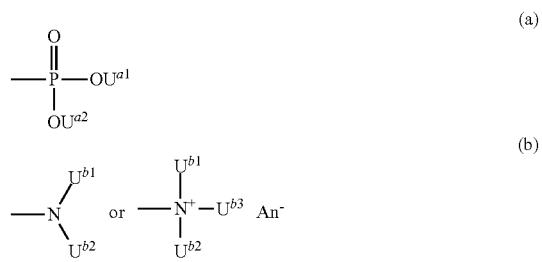

(wherein
$U^{a1}$, $U^{a2}$, $U^{b1}$, $U^{b2}$ and $U^{b3}$ each independently represent a hydrogen atom or a linear or branched alkyl group having 1 to 5 carbon atoms, and An represents an anion selected from the group consisting of a halide ion, an inorganic acid ion, a hydroxide ion and an isothiocyanate ion).

[7] The method for manufacturing the cell culture container described in [6], wherein the copolymer further has a recurring unit which contains a group represented by the following formula (c):

—R$^c$ (c)

[wherein
R$^c$ represents a linear or branched alkyl group having 1 to 18 carbon atoms, a cyclic hydrocarbon group having 3 to 10 carbon atoms, an aryl group having 6 to 10 carbon atoms, an aralkyl group having 7 to 15 carbon atoms or an aryloxyalkyl group having 7 to 15 carbon atoms (here, the above-mentioned aryl portion may be substituted by a linear or branched alkyl group having 1 to 5 carbon atoms which may be substituted by a halogen atom(s))].

[8] The cell culture container described in any one of [1] to [5], wherein transmittance in a visible light region is 90% or more.

[9] The cell culture container described in any one of [1] to [5], wherein a material thereof is glass, a metal containing compound, a semi-metal containing compound or a resin.

Effects of the Invention

The cell culture container of the present invention can inhibit adhesion of cells and proteins to the container surface by a copolymer having an anion represented by the formula (a), a cation represented by the formula (b) and a hydrophobic group represented by the formula (c) being coated onto at least a part of the surface thereof. It can be considered that, due to electrostatic balance between the cation and the anion, the surface of the container is maintained to electrically neutral, so that adhesion of the cells and the proteins can be prevented. On the other hand, since the cation and the anion in the coating form an ionic bond (ion complex), adhesion can be carried out without selecting a kind of the substrate of the container such as glass, fibers, inorganic particles or a resin (a synthetic resin and a natural resin), etc., and further, after adhesion, it becomes a coating excellent in durability to an aqueous solvent (water, phosphate-buffered saline (PBS), alcohol, etc.). Further, even in a cell culture container having a minute space, a cell culture container in which a coating film is formed uniformly onto the container surface without any defects such as bubble biting, etc., can be manufactured.

The cell culture container of the present invention is provided with a coating film containing a polymer having a function of inhibiting adhesion of biological substances, in particular, a copolymer having a specific anionic structure and a specific cationic structure onto at least a part of the surface with a difference between the maximum film thickness and the minimum film thickness of 1,000 Å or less, and preferably 300 Å or less. The coating film has an excellent function of inhibiting adhesion of biological substances. In addition, a coating film can be provided with a simple and easy operation to various kinds of materials such as glass, a metal containing compound or a semi-metal containing compound, activated charcoal, a resin, etc. In addition, in some cases, by introducing a hydrophobic group into the above-mentioned copolymer, a coating film having good adhesiveness to a resin such as plastics, etc., and excellent in durability to an aqueous solvent after adhesion can be provided.

Further, even if the cell culture container of the present invention is a material containing a structural portion constituted by at least two planes which are in contact with each other and an angle at which the two planes are crossed is 0<θ<180°, a thickness at an edge portion or bottom surface does not remarkably increased by accumulating the coating agent at the edge portion or bottom surface of such a structural portion, and a uniform and conformal coating film having a difference between the maximum film thickness and the minimum film thickness of 1,000 Å or less, preferably 300 Å or less can be provided. And a microwell plate provided with a uniform and conformal coating film having a difference between the maximum film thickness and the minimum film thickness of 1,000 Å or less, preferably 300 Å or less is useful not only in the point of having a sufficient function of inhibiting adhesion of biological substances but also in the point of not suffering an influence to the optical measurement since the film thickness is a measurement wavelength of a general plate reader (for example, 340 to 850 nm) or less.

EMBODIMENTS TO CARRY OUT THE INVENTION

1. Explanation of the Terms

Figure 1:
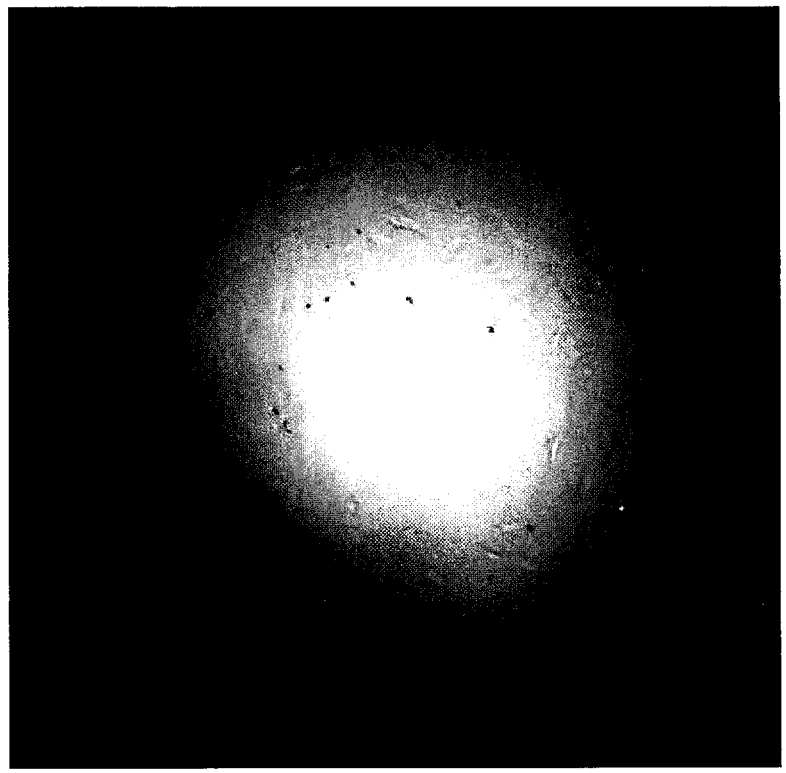
FIG. 1 is a photograph of observation results of negative control (Corning #3893) in (Table 1) by an inverted microscope.
Figure 2:
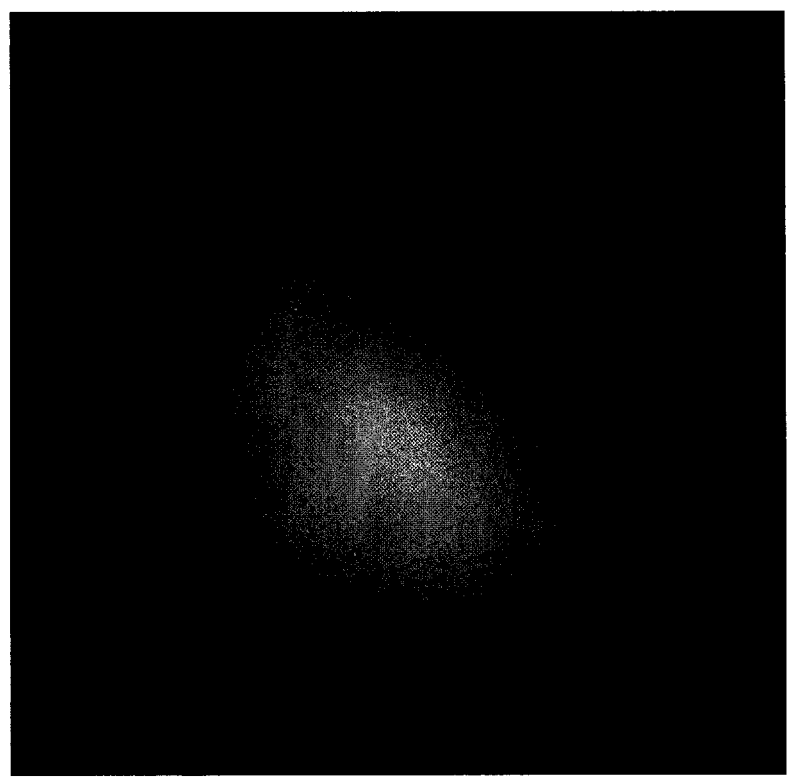
FIG. 2 is a photograph of observation results of Example 1 (Corning #3893) in (Table 1) by an inverted microscope.
Figure 3:
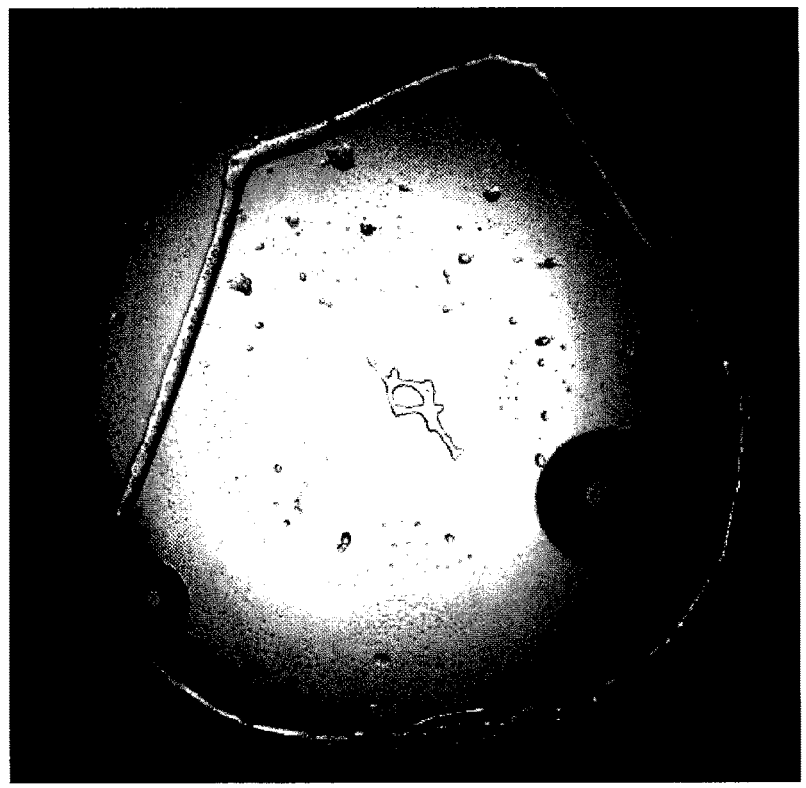
FIG. 3 is a photograph of observation results of Comparative example 1 (Corning #3893) in (Table 1) by an inverted microscope.
Figure 4:
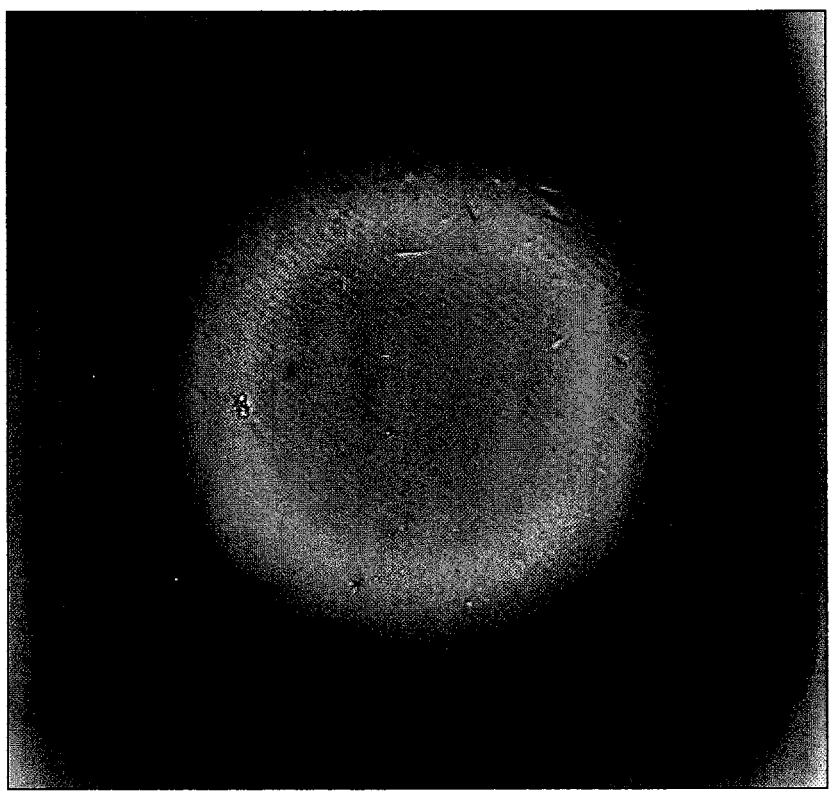
FIG. 4 is a photograph of observation results of negative control (Greiner #782180) in (Table 1) by an inverted microscope.
Figure 5:
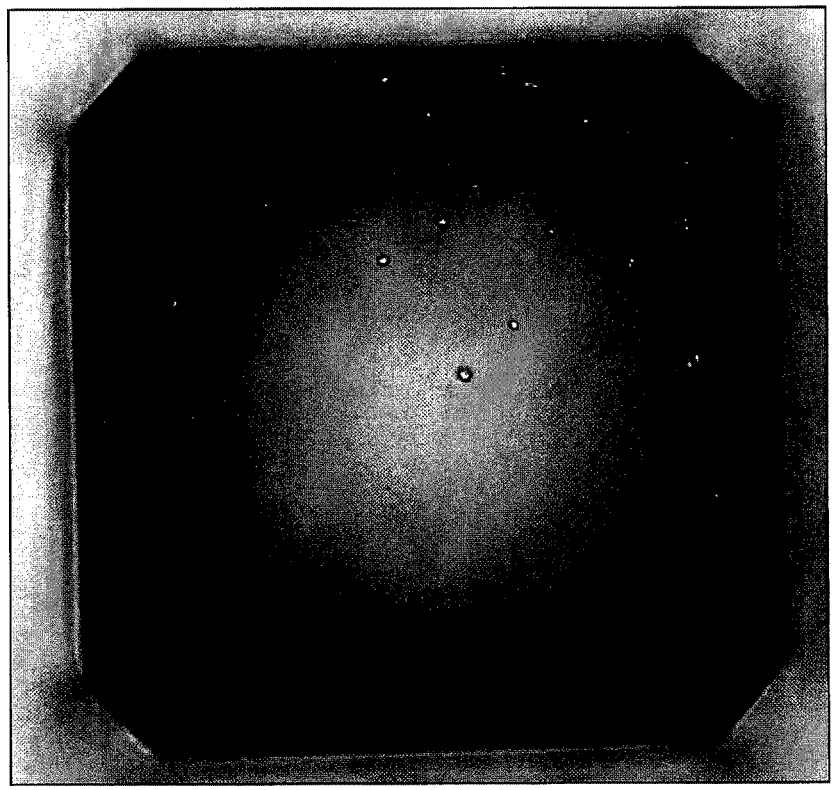
FIG. 5 is a photograph of observation results of Example 1 (Greiner #782180) in (Table 1) by an inverted microscope.
Figure 6:
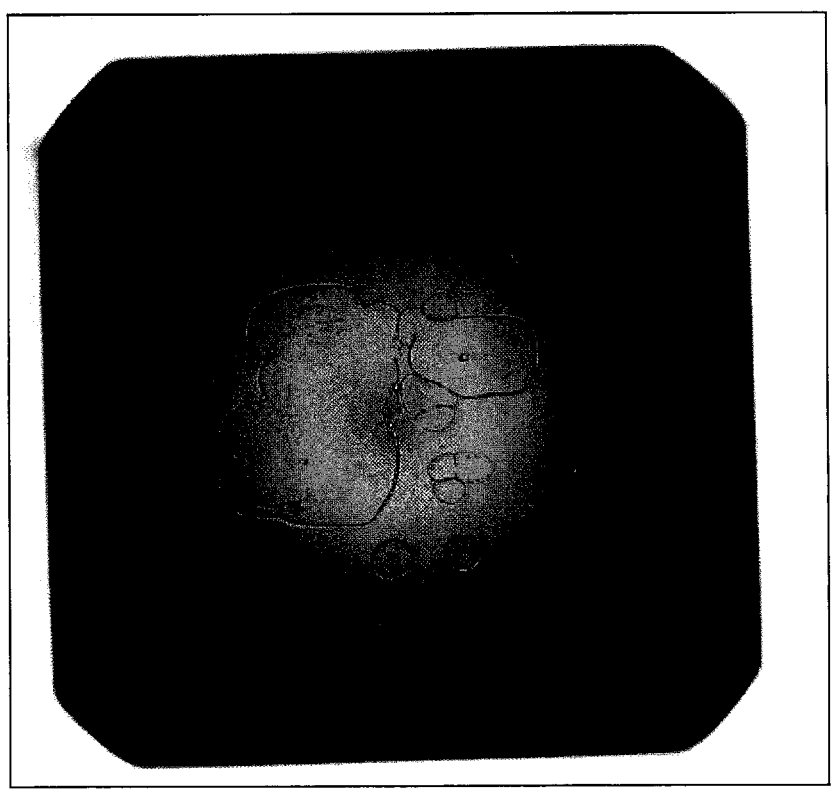
FIG. 6 is a photograph of observation results of Comparative example 1(Greiner #782180) in (Table 1) by an inverted microscope.

The terms used in the present invention have the following definitions, otherwise specifically mentioned.

In the present invention, the "halogen atom" means a fluorine atom, a chlorine atom, a bromine atom or an iodine atom.

In the present invention, the "alkyl group" means a linear or branched, saturated monovalent aliphatic hydrocarbon group. The "linear or branched alkyl group having 1 to 5 carbon atoms" may be mentioned, for example, a methyl group, an ethyl group, an n-propyl group, an isopropyl group, an n-butyl group, an isobutyl group, an s-butyl group, a t-butyl group, an n-pentyl group, a 1-methylbutyl group, a 2-methylbutyl group, a 3-methylbutyl group, a 1,1-dimethylpropyl group, a 1,2-dimethylpropyl group, a 2,2-dimethylpropyl group or a 1-ethylpropyl group. The "linear or branched alkyl group having 1 to 18 carbon atoms" may be mentioned, in addition to the examples of the "linear or branched alkyl group having 1 to 5 carbon atoms", a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group or an octadecyl group, or an isomer thereof.

In the present invention, the "linear or branched alkyl group having 1 to 5 carbon atoms which may be substituted by a halogen atom(s)" means either the above-mentioned linear or branched alkyl group having 1 to 5 carbon atoms, or the above-mentioned linear or branched alkyl group having 1 to 5 carbon atoms substituted by one or more of the above-mentioned halogen atoms. Examples of the "linear or branched alkyl group having 1 to 5 carbon atoms" are as mentioned above. On the other hand, the "linear or branched alkyl group having 1 to 5 carbon atoms substituted by one or more halogen atoms" means a group in which one or more optional hydrogen atoms of the above-mentioned linear or branched alkyl group having 1 to 5 carbon atoms is/are substituted by a halogen atom(s), and examples thereof may be mentioned a fluoromethyl group, a difluoromethyl group, a trifluoromethyl group, a chloromethyl group, a dichloromethyl group, a trichloromethyl group, a bromomethyl group, an iodomethyl group, a 2,2,2-trifluoroethyl group, a 2,2,2-trichloroethyl group, a perfluoroethyl group, a perfluorobutyl group or a perfluoropentyl group, etc.

In the present invention, the "ester bond" means —C(=O)—O— or —O—C(=O)—, the "amide bond" means —NHC(=O)— or —C(=O)NH— and the "ether bond" means —O—.

In the present invention, the "linear or branched alkylene group having 1 to 10 carbon atoms which may be substituted by a halogen atom(s)" means a linear or branched alkylene group having 1 to 10 carbon atoms or a linear or branched alkylene group having 1 to 10 carbon atoms substituted by one or more halogen atoms. Here, the "alkylene group" means a divalent organic group corresponding to the above-mentioned alkyl group. Examples of the "linear or branched alkylene group having 1 to 10 carbon atoms" may be mentioned a methylene group, an ethylene group, a propylene group, a trimethylene group, a tetramethylene group, a 1-methylpropylene group, a 2-methylpropylene group, a dimethylethylene group, an ethylethylene group, a pentamethylene group, a 1-methyl-tetramethylene group, a 2-methyl-tetramethylene group, a 1,1-dimethyl-trimethylene group, a 1,2-dimethyl-trimethylene group, a 2,2-dimethyl-trimethylene group, a 1-ethyl-trimethylene group, a hexamethylene group, an octamethylene group and a decamethylene group, etc., among these, an ethylene group, a propylene group, an octamethylene group and a decamethylene group are preferred, and, for example, a linear or branched alkylene group having 1 to 5 carbon atoms such as an ethylene group, a propylene group, a trimethylene group, a tetramethylene group, etc., are more preferred, and, in particular, an ethylene group or a propylene group is preferred. The "linear or branched alkylene group having 1 to 10 carbon atoms substituted by one or more halogen atoms" means a group in which one or more optional hydrogen atoms of the above-mentioned alkylene group is/are substituted by a halogen atom(s), and, in particular, a part or whole of the hydrogen atom(s) of the ethylene group or the propylene group is/are substituted by a halogen atom(s) is/are preferred.

In the present invention, the "alicyclic hydrocarbon group having 3 to 10 carbon atoms" means a monocyclic or polycyclic, saturated or partially unsaturated, monovalent aliphatic hydrocarbon group having 3 to 10 carbon atoms. Among these, a monocyclic or bicyclic, saturated monovalent aliphatic hydrocarbon group having 3 to 10 carbon atoms is preferred, and there may be mentioned, for example, a cycloalkyl group having 3 to 10 carbon atoms such as a cyclopropyl group, a cyclobutyl group and a cyclohexyl group, etc., or a bicycloalkyl group having 4 to 10 carbon atoms such as a bicyclo[3.2.1]octyl group, a bornyl group and an isobornyl group, etc.

In the present invention, the "aryl group having 6 to 10 carbon atoms" means a monocyclic or polycyclic, monovalent aromatic hydrocarbon group having 6 to 10 carbon atoms, and there may be mentioned, for example, a phenyl group, a naphthyl group or an anthryl group, etc. The "aryl group having 6 to 10 carbon atoms" may be substituted by one or more of the above-mentioned "linear or branched alkyl group having 1 to 5 carbon atoms which may be substituted by a halogen atom(s)."

In the present invention, the "aralkyl group having 7 to 15 carbon atoms" means a group —R—R' (here, R represents the above-mentioned "alkylene group having 1 to 5 carbon atoms", and R' represents the above-mentioned "aryl group having 6 to 10 carbon atoms"), and there may be mentioned, for example, a benzyl group, a phenethyl group or an α-methylbenzyl group, etc. The aryl portion of the "aralkyl group having 7 to 15 carbon atoms" may be substituted by one or more of the above-mentioned "linear or branched alkyl group having 1 to 5 carbon atoms which may be substituted by a halogen atom(s)."

In the present invention, the "aryloxyalkyl group having 7 to 15 carbon atoms" means a group —R—O—R' (here, R represents the above-mentioned alkylene group having 1 to 5 carbon atoms", and R' represents the above-mentioned "aryl group having 6 to 10 carbon atoms"), and there may be mentioned, for example, a phenoxymethyl group, a phenoxyethyl group or a phenoxypropyl group, etc. The aryl portion of the "aryloxyalkyl group having 7 to 15 carbon atoms" may be substituted by one or more of the above-mentioned "linear or branched alkyl group having 1 to 5 carbon atoms which may be substituted by a halogen atom(s)."

In the present invention, the "halide ion" means a fluoride ion, a chloride ion, a bromide ion or an iodide ion.

In the present invention, the "inorganic acid ion" means a carbonate ion, a sulfate ion, a phosphate ion, a hydrogen phosphate ion, a dihydrogen phosphate ion, a nitrate ion, a perchlorate ion or a borate ion.

As the above-mentioned $An^-$, preferred are a halide ion, a sulfate ion, a phosphate ion, a hydroxide ion and an isothiocyanate ion, and particularly preferred is a halide ion.

In the present invention, the (meth)acrylate compound means both of an acrylate compound and a methacrylate compound. For example, the (meth)acrylic acid means acrylic acid and methacrylic acid.

In addition, in the present invention, the "anion" or the "anionic group" means a negative ion or a negative ionic group, and also contains a group capable of becoming a negative ion or a negative ionic group by dissociating in water. Similarly, in the present invention, the "cation" or the "cationic group" means a positive ion or a positive ionic group, and also contains a group capable of becoming a positive ion or a positive ionic group by dissociating in water.

To have a function of inhibiting adhesion of cells means that, for example, relative absorbance (WST O.D.450 nm) (%) (absorbance of Example (WST O.D.450 nm)/absorbance of Comparative example (WST O.D. 450 nm)×100) when compared with no coating, by cell number measurement reagent carried out by the method described in Examples, is 50% or less, preferably 30% or less, and further preferably 20% or less.

To have a function of inhibiting adhesion of proteins means that, for example, a mass (%) per a relative unit area (a mass ($ng/cm^2$) per a unit area of Example/a mass ($ng/cm^2$) per a unit area of Comparative example×100) when compared with no coating, by QCM-D measurement carried out by the method described in Examples, is 50% or less, preferably 30% or less, and further preferably 20% or less.

In the present invention, the protein may be mentioned fibrinogen, bovine serum albumin (BSA), human albumin, various kinds of globulins, β-lipoprotein, various kinds of antibodies (IgG, IgA, IgM), peroxidases, various kinds of complements, various kinds of lectins, fibronectin, lysozyme, von Willebrand factor (vWF), serum γ-globulin, pepsin, ovalbumin, insulin, histone, ribonuclease, collagen, cytochrome c, etc., and in particular, it has particularly a high function of inhibiting adhesion of proteins (albumin and globulin) contained in serum.

2. Explanation of the Present Invention

<<Cell Culture Container>>

A first embodiment of the present invention is a cell culture container having at least one opened minute space with a volume of 20 μL or less on the surface of the container, and provided with a coating film containing a copolymer having a recurring unit which contains a group represented by the following formula (a) and a recurring unit which contains a group represented by the following formula (b):

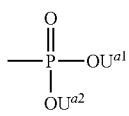

(a)

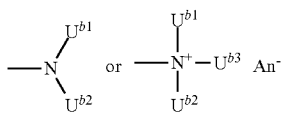

(b)

(wherein
$U^{a1}$, $U^{a2}$, $U^{b1}$, $U^{b2}$ and $U^{b3}$ each independently represent a hydrogen atom or a linear or branched alkyl group having 1 to 5 carbon atoms, and An represents an anion selected from the group consisting of a halide ion, an inorganic acid ion, a hydroxide ion and an isothiocyanate ion).
onto at least a part of the surface portion of the container constituting the minute space.

It is preferably a cell culture container, wherein the above-mentioned copolymer further has a recurring unit which contains a group represented by the following formula (c):

$$—R^c \quad\quad (c)$$

[wherein,
$R^c$ represents a linear or branched alkyl group having 1 to 18 carbon atoms, a cyclic hydrocarbon group having 3 to 10 carbon atoms, an aryl group having 6 to 10 carbon atoms, an aralkyl group having 7 to 15 carbon atoms or an aryloxyalkyl group having 7 to 15 carbon atoms (here, the above-mentioned aryl portion may be substituted by a linear or branched alkyl group having 1 to 5 carbon atoms which may be substituted by a halogen atom(s))].

<Cell>

The cell in the present invention is the most basic unit constituting an animal or plant, and has a cytoplasm and various kinds of cytoplasmic organelles inside a cell membrane as its elements. At this time, the nucleus including DNA may or may not be contained inside the cell. For example, in the cells derived from an animal in the present invention, germ cells such as sperm cells and egg cells, somatic cells constituting a living body, stem cells (multipotent stem cells, etc.), progenitor cells, cancer cells isolated from a living body, cells (cell lines) isolated from a living body and stably maintained ex vivo by acquiring immortality, cells isolated from a living body and artificially subjected to genetic modification, cells isolated from a living body and the nucleus of which is artificially exchanged, etc., are contained. Examples of the somatic cells constituting a living body are not limited to the following, and include fibroblast, bone marrow cells, B lymphocytes, T lymphocytes, neutrophils, erythrocytes, platelets, macrophages, monocytes, bone cells, bone marrow cells, pericytes, dendritic cells, keratinocytes, adipocytes, mesenchymal cells, epithelial cells, epidermal cells, endothelial cells, vascular endothelial cells, hepatic parenchymal cells, cartilage cells, cumulus cells, neural cells, glial cells, neurons, oligodendrocytes, microglia, astroglial cells, cardiomyocytes, esophagus cells, muscle cells (for example, smooth muscle cells or skeletal muscle cells), pancreatic beta cells, melanocytes, hematopoietic progenitor cells (for example, CD34-positive cells derived from umbilical cord blood), and mononuclear cells, etc. The somatic cells include, for example, cells isolated from optional tissues such as skin, kidney, spleen, adrenal gland, liver, lung, ovary, pancreas, uterus, stomach, colon, small intestine, large intestine, bladder, prostate, testis, thymus, muscle, connective tissue, bone, cartilage, blood vessel tissue, blood (including umbilical cord blood), bone marrow, heart, eye, brain or nerve tissue, etc. The stem cell is a cell having both of an ability to replicate itself and an ability to differentiate into cells of other multiple lineages, and examples thereof include, while it is not limited to the following, embryonic stem cells (ES cell), embryonic tumor cells, embryonic germ stem cells, induced pluripotent stem cells (iPS cell), neural stem cells, hematopoietic stem cells, mesenchymal stem cells, hepatic stem cells, pancreatic stem cells, muscle stem cells, germ stem cells, intestinal stem cells, cancer stem cells, hair follicle stem cells, etc.

As the multipotent stem cells, among the above-mentioned stem cells, ES cells, embryonic germ stem cells and iPS cells are mentioned. The progenitor cells are cells that are in the course of being differentiated from the above-mentioned stem cells into specific somatic cells or germ cells. The cancer cells are cells that have acquired unlimited proliferative capacity by deriving from somatic cells. The cell lines are cells that have acquired unlimited proliferative capacity by artificial manipulation in vitro.

Examples of the cancer cell lines may be mentioned, while it is not limited to the following, HBC-4, BSY-1, BSY-2, MCF-7, MCF-7/ADR RES, HS578T, MDA-MB-231, MDA-MB-435, MDA-N, BT-549 and T47D as human breast cancer cell lines, HeLa as human cervical cancer cell lines, A549, EKVX, HOP-62, HOP-92, NCI-H23, NCI-H226, NCI-H322M, NCI-H460, NCI-H522, DMS273 and DMS114 as human lung cancer cell lines, Caco-2, COLO-205, HCC-2998, HCT-15, HCT-116, HT-29, KM-12, SW-620 and WiDr as human colon cancer cell lines, DU-145, PC-3 and LNCaP as human prostatic cancer cell lines, U251, SF-295, SF-539, SF-268, SNB-75, SNB-78 and SNB-19 as human central nervous system cancer cell lines, OVCAR-3, OVCAR-4, OVCAR-5, OVCAR-8, SK-OV-3 and IGROV-1 as human ovarian cancer cell lines, RXF-631L, ACHN, UO-31, SN-12C, A498, CAKI-1, RXF-393L, 786-0 and TK-10 as human renal cancer cell lines, MKN45, MKN28, St-4, MKN-1, MKN-7 and MKN-74 as human stomach cancer cell lines, LOX-IMVI, LOX, MALME-3M, SK-MEL-2, SK-MEL-5, SK-MEL-28, UACC-62, UACC-257 and M14 as skin cancer cell lines, and CCRF-CRM, K562, MOLT-4, HL-60TB, RPMI8226, SR, UT7/TPO and Jurkat as leukemia cell lines, etc. Examples of the cell lines may be mentioned, while it is not limited to the following, HEK293 (Human Embryonic Kidney cells), MDCK, MDBK, BHK, C-33A, AE-1, 3D9, Ns0/1, NIH3T3, PC12, S2, Sf9, Sf21, High Five (Registered Trademark) and Vero, etc. Examples of the human liver cell lines may be mentioned, while it is not limited to the following, HepG2, Hep3B, HepaRG (Registered Trademark), JHH7, HLF, HLE, PLC/PRF/5, WRL68, HB611, SK-HEP-1, HuH-4 and HuH-7, etc.

In the plant-derived cells in the present invention, cells isolated from each tissue of the plant body are included, and protoplasts obtained by artificially removing cell walls from the cells are also included.

<Container>

The container to which the copolymer is coated, which constitutes the cell culture container of the present invention, may be containers with an optional shape capable of using in this field of the art, and may be mentioned, for example, dishes/schale generally used for cell culture such as petri dish dishes, dishes for tissue culture, multi dishes, etc., flasks such as a cell culture flask, a spinner flask, etc., bags such as plastic bags, Teflon (Registered Trademark) bags, culture bags, etc., multi-well plates such as multi dishes/multi-plates, microplates/microwell plates, deep well plates, etc., slide glass such as chamber slide, etc., and related products, tubes such as culture tubes, centrifuge tubes, microtubes, etc., trays, roller bottles and the like. It is preferably mentioned 6 to 1536 well multi-well plates and dishes/schale.

The container of the present invention has one or more opened minute spaces on the surface thereof. The minute space means, for example, a well (hole) or dimple (depression) with an arbitrary shape provided in a plate, dish/schale, etc., and a volume thereof is 20 µL or less per one minute space, preferably 0.1 to 20 µL, and typically 5 to 20 µL. As a use thereof, for example, it is used for manufacture of cell aggregates. Specifically, there may be mentioned a 1536 well multi-well plate, a dimple schale (petri dish), a commercially available plate for culturing cells with a large amount, having a volume per 1 well (1 hole) of 5 to 20 µL, for manufacturing a large amount of cell aggregates.

For example, in the above-mentioned plate (cell culture container), minute spaces for culturing cells are continuously arranged side by side (for example, see FIG. 7 and FIG. 8), and in the usual coating type coating film, problems such as bubble biting or ununiform film thickness, etc., occur. The cell culture container of the present application is provided with a coating film which does not cause bubble biting of the coating film and is uniform in a film thickness at least a part of the container surface.

The container may be a material in which the top is opened (typically, schale (petri dish), dish, etc.), or a material in which it is sealed (flask, bag), and for convenience of coating the coating agent of the present application, it is typically suitable for a cell culture container in which the top is opened.

Here, a shape of the minute space (well, dimple, etc.) possessed by the above-mentioned cell culture container may be substantially hemispherical, substantially rectangular parallelepiped or substantially cylindrical, and the bottom surface thereof may be flat or round. For example, when the shape of each well is a substantially rectangular parallelepiped shape or a substantially cylindrical shape, the above-mentioned "at least two planes which are in contact with each other" are the inner surface of the bottom surface and the inner surface of the wall surface of the well, and the above-mentioned "angle θ at which two planes are crossed" means an angle constituted by the inner surface of the bottom surface and the inner surface of the wall surface of the each well. When the bottom surface is a round bottom, the above-mentioned "inner surface of the bottom surface" can be replaced with a tangential plane at the lowermost bottom portion of the round bottom. Further, when the shape of each well is substantially hemispherical, the above-mentioned "at least two planes which are in contact with each other" can be replaced with a tangential plane at the lowermost bottom portion of the hemispherical well and a tangential plane at the midpoint of the arc from the lowermost bottom portion to the end portion, and the above-mentioned "angle θ at which two planes are crossed" means an angle constituted by the above-mentioned two tangential planes.

As the material of the container, typically, glass or a resin can be used. From the viewpoints of processability and economy, etc., a resin is preferably used. The resin may be either of a natural resin or a synthetic resin, as the natural resin, there may be mentioned, for example, cellulose, cellulose triacetate (CTA), cellulose to which dextran sulfate has been fixed, etc., and as the synthetic resin, there may be mentioned, for example, polyacrylonitrile (PAN), polyester-based polymer alloy (PEPA), polystyrene (PS), polysulfone (PSF), polyethylene terephthalate (PET), polymethyl methacrylate (PMMA), polyvinyl alcohol (PVA), polyurethane (PU), ethylene vinyl alcohol (EVAL), polyethylene (PE), polyester, polypropylene (PP), polyvinylidene fluoride (PVDF), polyether sulfone (PES), polycarbonate (PC), polyvinyl chloride (PVC), polytetrafluoroethylene (PTFE), ultra high molecular weight polyethylene (UHPE), polydimethylsiloxane (PDMS), acrylonitrile-butadiene-styrene resin (ABS), Teflon (Registered Trademark), cycloolefin polymer (COP) (for example, ZEONOR (Registered Trademark), ZEONEX (Registered Trademark) (available from ZEON CORPORATION) or various kinds of ion exchange resin. etc. In the manufacture of the cell culture container of the present invention, at the time of coating the copolymer to exist at least a part of the surface of the container, it is not necessary to treat it at a high temperature, so that a resin having low heat resistance, etc., can be applied.

As the material of the container of the present invention, a metal containing compound or a semi-metal containing compound may be used. The metal may be mentioned a typical metal: (an alkali metal: Li, Na, K, Rb, Cs; an alkaline earth metal: Ca, Sr, Ba, Ra), a magnesium group element: Be, Mg, Zn, Cd, Hg; an aluminum group element: Al, Ga, In; a rare earth element: Y, La, Ce, Pr, Nd, Sm, Eu; a tin group element: Ti, Zr, Sn, Hf, Pb, Th; an iron group element: Fe, Co, Ni; a vanadium group element: V, Nb, Ta, a chromium group element: Cr, Mo, W, U; a manganese group element: Mn, Re; a noble metal: Cu, Ag, Au; and a platinum group element: Ru, Rh, Pd, Os, Ir, Pt, etc. The metal containing compound or the semi-metal containing compound may be mentioned, for example, ceramics comprising a metal oxide as a basic component, which are a sintered body baked by a heat treatment at a high temperature, a semiconductor such as silicon, an inorganic solid material including a molded product of an inorganic compound such as a metal oxide or a semi-metal oxide (silicon oxide, alumina, etc.), a metal carbide or a semi-metal carbide, a metal nitride or a semi-metal nitride (silicon nitride, etc.), a metal boride or a semi-metal boride, etc., aluminum, nickel-titanium and stainless (SUS304, SUS316, SUS316L, etc.).

The cell culture container of the present invention is provided with a coating film having a difference between the maximum film thickness and the minimum film thickness of 1,000 Å or less, preferably 300 Å or less, more preferably 100 Å or less onto at least a part of the surface portion of the container constituting the minute space.

The above-mentioned cell culture container is constituted by at least two planes in contact with each other, and may contain a structural portion in which an angle θ at which the two planes are crossed is 0<θ<180°, preferably 30°<θ<150°, particularly 70°<θ<110°. Incidentally, one of the planes or a part or whole of the both planes may be a curved surface. When the cell culture container having such a structural portion is coated by the conventional technology, there is a drawback that accumulation of the coating agent is generated at the edge portion having the above-mentioned angle θ or the bottom surface, but when the coating film particularly contains a copolymer having a recurring unit which contains a group represented by the above-mentioned formula (a), a recurring unit which contains a group represented by the above-mentioned formula (b), and in some cases, a recurring unit which contains a group represented by the above-mentioned formula (c), such a drawback can be avoided.

The coating film of the present application may be applied to laboratory equipment, analytical equipment or medical equipment. In particular, in the laboratory equipment, analytical equipment or medical equipment, it may be whole equipment to be used in contact with in vivo tissue or blood, or at least a part of the structural material thereof. Examples of the laboratory equipment may be mentioned the cell culture container mentioned above. Examples of the medical equipment may be mentioned whole or at least a part thereof of structural materials such as in vivo implantable type prosthetic organs and treatment devices, extracorporeal circulation type prosthetic organs, catheters, tubes, prosthetic valves, stents, prosthetic joints, etc.

In particular, as the substrate for optical measurement, it is not particularly limited as long as it is a substrate (a base material) to be supplied to optical measurement, and may be mentioned, for example, the above-mentioned structural substrate to be supplied for optical measurement (measurement wavelength is, for example, 340 to 850 nm) and in addition to these, for example, a substrate (a base material) (a cell culture plate, etc.) used for a plate reader, a plate for a phase contrast microscope, a cell for UV measurement, a transparent electrode (an ITO electrode) or the like.

The cell culture container of the present invention desirably has transmittance in a visible light region in the minute space provided with the coating film of 90% or more, preferably 92% or more, preferably 95% or more, and most preferably 98% or more.

<Copolymer>

The cell culture container of the present invention is characterized in that it has at least one opened minute space having a volume of 20 μL or less onto the surface of the container, and at least a part of the surface portion of the container constituting the minute space is coated by a specific copolymer. The copolymer according to the present invention is a copolymer having
a recurring unit which contains a group represented by the following formula (a) and a recurring unit which contains a group represented by the following formula (b):

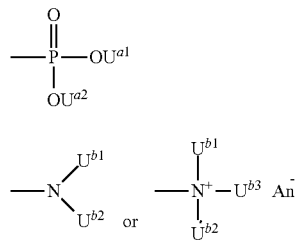

(a)

(b)

(wherein
$U^{a1}$, $U^{a2}$, $U^{b1}$, $U^{b2}$ and $U^{b3}$ each independently represent a hydrogen atom or a linear or branched alkyl group having 1 to 5 carbon atoms, and An⁻ represents an anion selected from the group consisting of a halide ion, an inorganic acid ion, a hydroxide ion and an isothiocyanate ion).

The above-mentioned copolymer may further have a recurring unit containing a group represented by the following formula (c):

(c)

[wherein,
$R^c$ represents a linear or branched alkyl group having 1 to 18 carbon atoms, a cyclic hydrocarbon group having 3 to 10 carbon atoms, an aryl group having 6 to 10 carbon atoms, an aralkyl group having 7 to 15 carbon atoms or an aryloxyalkyl group having 7 to 15 carbon atoms (here, the above-mentioned aryl portion may be substituted by a linear or branched alkyl group having 1 to 5 carbon atoms which may be substituted by a halogen atom(s))].

The copolymer according to the present invention is not particularly limited as long as it is a copolymer having a recurring unit which contains a group represented by the above-mentioned formula (a), a recurring unit which contains a group represented by the above-mentioned formula (b), and preferably further having a recurring unit which contains a group represented by the above-mentioned formula (c). Incidentally, in the present invention, the recurring unit which contains a group represented by the above-mentioned formula (c) is different from the recurring unit which contains a group represented by the above-mentioned formula (a) and the recurring unit which contains a group represented by the above-mentioned formula (b). The copolymer is desirably a material obtained by subjecting to radical polymerization of a monomer which contains a group represented by the above-mentioned formula (a), a monomer which contains a group represented by the above-mentioned formula (b), and a monomer which contains a group represented by the above-mentioned formula (c), and it is also possible to use a material obtained by subjecting to polycondensation or polyaddition reaction. Examples of the copolymer may be mentioned a vinyl polymerized polymer in which olefins are reacted, polyamide, polyester, polycarbonate, polyurethane, etc., and among these, a vinyl polymerized polymer in which olefins are reacted or a (meth)acrylic polymer in which (meth)acrylate compounds are polymerized is particularly desirable.

The monomers which contain a group represented by the above-mentioned formulae (a), (b) and (c) are each preferably monomers represented by the following formulae (A), (B) and (C):

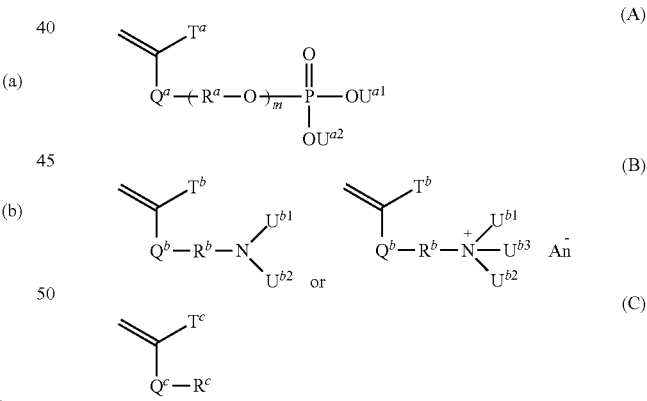

[wherein,
$T^a$, $T^b$, $T^c$, $U^{a1}$, $U^{a2}$, $U^{b1}$, $U^{b2}$ and $U^{b3}$ each independently represent a hydrogen atom or a linear or branched alkyl group having 1 to 5 carbon atoms;
$Q^a$ and $Q^b$ each independently represent a single bond, an ester bond or an amide bond, $Q^c$ represents a single bond, an ether bond or an ester bond;
$R^a$ and $R^b$ each independently represent a linear or branched alkylene group having 1 to 18 carbon atoms which may be substituted by a halogen atom(s), $R^c$ represents a linear or branched alkyl group having 1 to 18 carbon atoms, an alicyclic hydrocarbon group having 3 to 10 carbon atoms, an aryl group having 6 to 10 carbon atoms, an aralkyl group having 7 to 15 carbon atoms or an aryloxyalkyl group having 7 to 15 carbon atoms (here, the above-mentioned aryl portion may be substituted by a linear or branched alkyl group having 1 to 5 carbon atoms which may be substituted by a halogen atom(s)); An⁻ represents an anion selected from the group consisting of a halide ion, an inorganic acid ion, a hydroxide ion and an isothiocyanate ion; and m represents an integer of 0 to 6], respectively. Accordingly, the recurring units derived from the monomers represented by the formulae (A), (B) and (C) are represented by the following formulae (a1), (b1) and (c1):

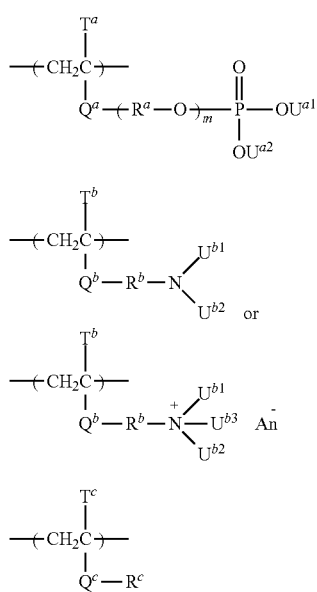

(wherein $T^a$, $T^b$, $T^c$, $U^{a1}$, $U^{a2}$, $U^{b1}$, $U^{b2}$ and $U^{b3}$, $Q^a$, $Q^b$, and $Q^c$, $R^a$, $R^b$ and $R^c$, An⁻ and m have the same meanings as defined above), respectively.

$T^a$, $T^b$ and $T^c$ preferably each independently represent a hydrogen atom, a methyl group or an ethyl group, and more preferably each independently represent a hydrogen atom or a methyl group.

$U^{a1}$, $U^{a2}$, $U^{b1}$, $U^{b2}$ and $U^{b3}$ preferably each independently represent a hydrogen atom, a methyl group, an ethyl group or a t-butyl group. $U^{a1}$ and $U^{a2}$ are more preferably hydrogen atoms. $U^{b1}$ and $U^{b2}$ (and $U^{b3}$) are more preferably a methyl group or an ethyl group, and particularly preferably a methyl group.

$Q^a$ and $Q^b$ preferably each independently represent an ester bond (—C(=O)—O— or —O—C(=O)—) or an amide bond (—NHC(=O)— or —C(=O)NH—), more preferably each independently represent —C(=O)—O— or —C(=O)NH—, and particularly preferably —C(=O)—O—. $Q^C$ preferably represents an ether bond or an ester bond (—C(=O)—O— or —O—C(=O)—), more preferably —O— or —C(=O)—O—, and particularly preferably —C(=O)—O—.

$R^a$ and $R^b$ preferably each independently represent a linear or branched alkylene group having 1 to 3 carbon atoms which may be substituted by a halogen atom(s), more preferably each independently represent an ethylene group or a propylene group, or an ethylene group or a propylene group substituted by one chlorine atom, and particularly preferably an ethylene group or a propylene group. $R^c$ preferably represents a linear or branched alkyl group having 4 to 8 carbon atoms or an alicyclic hydrocarbon group having 3 to 8 carbon atoms, more preferably a linear or branched alkyl group having 4 to 6 carbon atoms or an alicyclic hydrocarbon group having 3 to 6 carbon atoms, and particularly preferably a butyl group or a cyclohexyl group.

The above-mentioned An is preferably a halide ion, a sulfate ion, a phosphate ion, a hydroxide ion and an isothiocyanate ion, and particularly preferred is a halide ion.

In the formulae (A) and (B), m preferably represents an integer of 0 to 3, more preferably represents an integer of 1 or 2, and particularly preferably 1.

Specific examples of the above-mentioned formula (A) may be mentioned vinylphosphonic acid, acid phosphoxyethyl (meth)acrylate, 3-chloro-2-acid phosphoxypropyl (meth)acrylate, acid phosphoxypropyl (meth)acrylate, acid phosphoxymethyl (meth)acrylate, acid phosphoxypolyoxyethylene glycol mono(meth)acrylate, acid phosphoxypolyoxypropylene glycol mono(meth)acrylate, etc., and among these, vinylphosphonic acid and acid phosphoxyethyl methacrylate (=2-(methacryloyloxy)ethyl phosphate) are preferably used.

The structural formulae of vinylphosphonic acid, acid phosphoxyethyl methacrylate (=2-(methacryloyloxy)ethyl phosphate), acid phosphoxypolyoxyethylene glycol monomethacrylate and acid phosphoxypolyoxypropylene glycol monomethacrylate are represented by the following formula (A-1) to the formula (A-4), respectively.

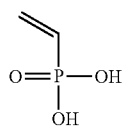
(A-1)

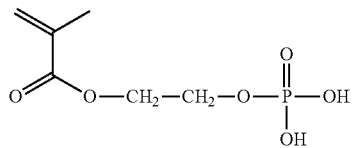
(A-2)

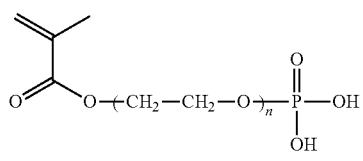
n = 4-5
(A-3)

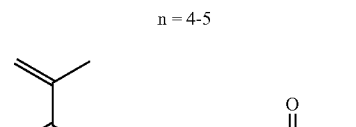
n = 5-6
(A-4)

These compounds may contain a (meth)acrylate compound having two functional groups as represented by the general formula (D) or (E) mentioned later at the time of synthesis in some cases.

Specific examples of the above-mentioned formula (B) may be mentioned dimethylaminoethyl (meth)acrylate, diethylaminoethyl (meth)acrylate, dimethylaminopropyl (meth)acrylate, 2-(t-butylamino)ethyl (meth)acrylate, methacryloylcholine chloride, etc., and among these, dimethylaminoethyl (meth)acrylate, methacryloylcholine chloride or 2-(t-butylamino)ethyl (meth)acrylate is preferably used.

The structural formulae of dimethylaminoethyl acrylate (=acrylic acid 2-(dimethylamino)ethyl), diethylaminoethyl methacrylate (=methacrylic acid 2-(diethylamino)ethyl), dimethylaminoethyl methacrylate (=methacrylic acid 2-(dimethylamino)ethyl), methacryloylcholine chloride and 2-(t-butylamino)ethyl methacrylate (=methacrylic acid 2-(t-butylamino)ethyl) are represented by the following formula (B-1) to the formula (B-5), respectively.

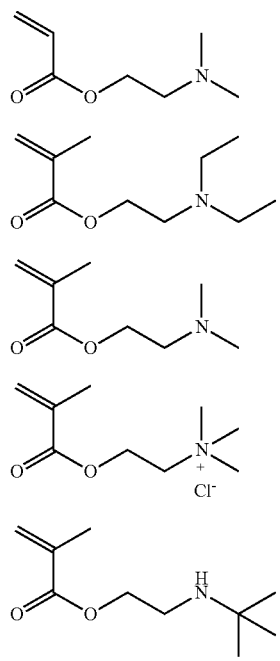

Specific examples of the above-mentioned formula (C) may be mentioned linear or branched alkyl esters of a (meth)acrylic acid such as butyl(meth)acrylate, 2-ethylhexyl (meth)acrylate, lauryl (meth)acrylate, stearyl (meth)acrylate, etc.; cyclic alkyl esters of a (meth)acrylic acid such as cyclohexyl (meth)acrylate, isobornyl (meth)acrylate, etc.; aralkyl esters of a (meth)acrylic acid such as benzyl (meth) acrylate, phenethyl (meth)acrylate, etc.; styrene-based monomers such as styrene, methylstyrene, chloromethylstyrene, etc.; vinyl ether-based monomers such as methyl vinyl ether, butyl vinyl ether, etc.; and vinyl ester-based monomers such as vinyl acetate, vinyl propionate, etc. Among these, butyl(meth)acrylate or cyclohexyl (meth)acrylate is preferably used.

The structural formulae of butyl methacrylate (=methacrylic acid butyl) and cyclohexyl methacrylate (=methacrylic acid cyclohexyl) are represented by the following formula (C-1) and the formula (C-2), respectively.

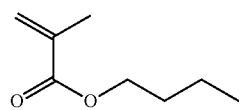

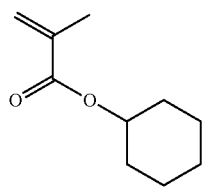

A ratio of the recurring unit which contains a group represented by the formula (a) (or a recurring unit represented by the formula (a1)) contained in the copolymer according to the present invention is 3 mol % to 80 mol %, preferably 3.5 mol % to 50 mol %, and further preferably 4 mol % to 40 mol %. Incidentally, the copolymer according to the present invention may contain two or more kinds of the recurring units represented by the formula (a) (or a recurring unit represented by the formula (a1)).

A ratio of the recurring unit which contains a group represented by the formula (b) (or a recurring unit represented by the formula (b1)) contained in the copolymer according to the present invention is 3 mol % to 80 mol %, preferably 5 mol % to 70 mol %, and further preferably 8 mol % to 65 mol %. Incidentally, the copolymer according to the present invention may contain two or more kinds of the recurring units represented by the formula (b) (or a recurring unit represented by the formula (b1)).

A ratio of the recurring unit which contains a group represented by the formula (c) (or a recurring unit represented by the formula (c1)) contained in the copolymer according to the present invention may be the whole reminder by subtracting the above-mentioned formula (a) and formula (b) from the whole copolymer, or may be the reminder subtracting the total ratio of the above-mentioned formula (a) and formula (b) and the fourth component described below, and it is, for example, 0 mol % to 90 mol %, preferably 3 mol % to 88 mol %, and further preferably 5 mol % to 87 mol %. Incidentally, the copolymer according to the present invention may contain two or more kinds of the recurring units represented by the formula (c) (or a recurring unit represented by the formula (c1)).

A combination of a ratio of the recurring units represented by the above-mentioned formula (a1), the formula (b1) and the formula (c1) in the copolymer according to the present invention is
preferably
3 mol % to 80 mol % of the formula (a1), 3 mol % to 80 mol % of the formula (b1), and 0 mol % to 90 mol % of the formula (c1),
more preferably
3.5 mol % to 50 mol % of the formula (a1), 5 mol % to 70 mol % of the formula (b1), and 3 mol % to 88 mol % of the formula (c1),
further preferably
4 mol % to 40 mol % of the formula (a1), 8 mol % to 65 mol % of the formula (b1), and 5 mol % to 87 mol % of the formula (c1).

Further, with the copolymer according to the present invention, an optional fourth component may be copolymerized. For example, as the fourth component, a (meth)acrylate compound having two or more functional groups is copolymerized, and a part of the polymer may be partially three-dimensionally crosslinked. Such a fourth component may be mentioned, for example, a bifunctional monomer represented by the following formula (D) or (E):

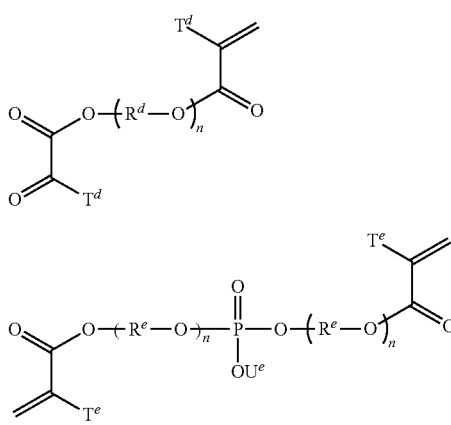

(D)

(E)

[wherein, $T^d$, $T^e$ and $U^e$ each independently represent a hydrogen atom or a linear or branched alkyl group having 1 to 5 carbon atoms, $R^d$ and $R^e$ each independently represent a linear or branched alkylene group having 1 to 10 carbon atoms which may be substituted by a halogen atom(s); and n represents an integer of 1 to 6]. That is, the copolymer according to the present invention preferably contains a crosslinking structure derived from such a bifunctional monomer.

In the formulae (D) and (E), $T^d$ and $T^e$ preferably each independently represent a hydrogen atom, a methyl group or an ethyl group, more preferably each independently represent a hydrogen atom or a methyl group.

In the formula (E), $U^e$ preferably represents a hydrogen atom, a methyl group or an ethyl group, and more preferably a hydrogen atom.

In the formula (D), $R^d$ preferably represents a linear or branched alkylene group having 1 to 3 carbon atoms which may be substituted by a halogen atom(s), more preferably each independently represent an ethylene group or a propylene group, or an ethylene group or a propylene group substituted by one chlorine atom, particularly preferably an ethylene group or a propylene group. In addition, in the formula (D), n preferably represents an integer of 1 to 5, and particularly preferably 1.

In the formula (E), $R^e$ preferably represents a linear or branched alkylene group having 1 to 3 carbon atoms which may be substituted by a halogen atom(s), more preferably each independently represent an ethylene group or a propylene group, or an ethylene group or a propylene group substituted by one chlorine atom, particularly preferably an ethylene group or a propylene group. Also, in the formula (E), n preferably represents an integer of 1 to 5, and particularly preferably 1.

The bifunctional monomer represented by the formula (D) may be preferably mentioned ethylene glycol di(meth)acrylate, triethylene glycol di(meth)acrylate, propylene glycol di(meth)acrylate, or a bifunctional monomer derived from the above-mentioned formula (A-3), etc.

The bifunctional monomer represented by the formula (E) may be preferably mentioned bis(methacryloyloxymethyl) phosphate, bis[(2-methacryloyloxy) ethyl] phosphate, bis[3-(methacryloyloxy)propyl] phosphate, or a bifunctional monomer derived from the above-mentioned formula (A-3).

The optional fourth component may be a trifunctional monomer. Such a trifunctional monomer as the fourth component may be mentioned, for example, phosphinylidynetris (oxy-2,1-ethanediyl) triacrylate.

Among these fourth components, in particular, among ethylene glycol dimethacrylate, and the bi-functional monomer derived from the above-mentioned formulae (A-3) and (A-4), a dimethacrylate having a recurring unit of ethylene glycol and propylene glycol, and among bis[2-(methacryloyloxy)ethyl] phosphate and the bi-functional monomer derived from the above-mentioned formulae (A-3) and (A-4), a dimethacrylate having a recurring unit of ethylene glycol and propylene glycol through a phosphate ester group is preferable, and the structural formulae thereof are represented by the following formulae (D-1) to (D-3) and formulae (E-1) to (E-3), respectively.

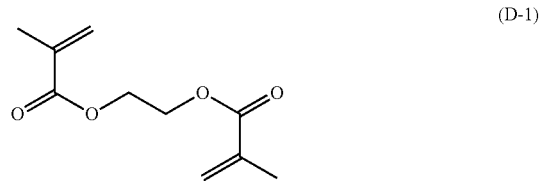

(D-1)

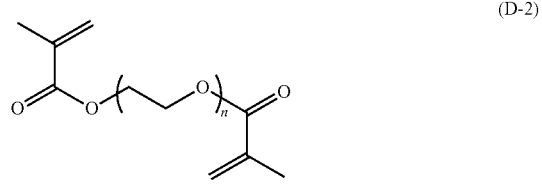

(D-2)

n = 4-5

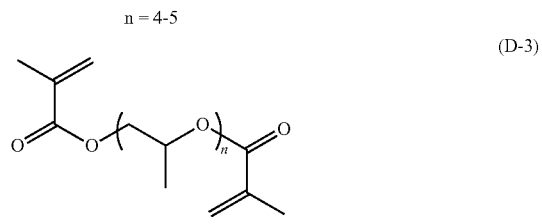

(D-3)

n = 5-6

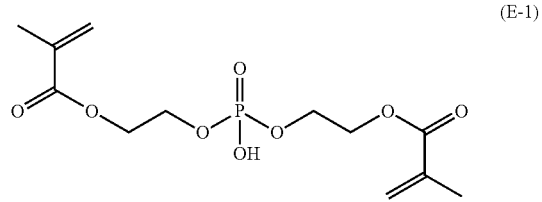

(E-1)

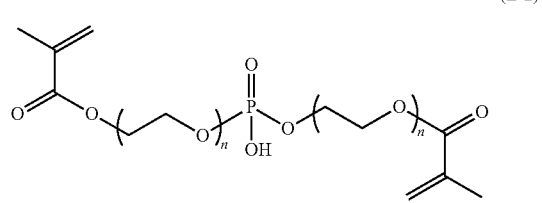

(E-2)

n = 4-5

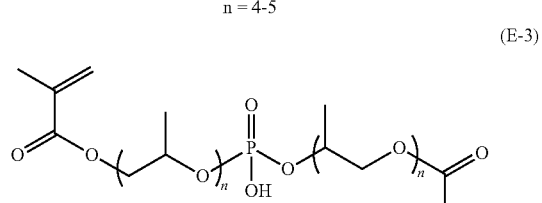

(E-3)

n = 5-6

In the copolymer, one kind or two or more kinds of these fourth components may be contained.

A ratio of the fourth component, for example, the cross-linking structure derived from bi-functional monomer represented by the above-mentioned formula (D) or (E) in the above-mentioned copolymer is 0 mol % to 50 mol %.

A ratio of the compound represented by the formula (A) in the whole monomer forming the above-mentioned copolymer is 3 mol % to 80 mol %, preferably 3.5 mol % to 50 mol %, and further preferably 4 mol % to 40 mol %. In addition, the compound represented by the formula (A) may be two or more kinds.

A ratio of the compound represented by the formula (B) in the whole monomer forming the above-mentioned copolymer is 3 mol % to 80 mol %, preferably 5 mol % to 70 mol %, and further preferably 8 mol % to 65 mol %. In addition, the compound represented by the formula (B) may be two or more kinds.

A ratio of the compound represented by the formula (C) in the whole monomer forming the above-mentioned copolymer may be the whole reminder subtracting the ratio of the above-mentioned formulae (A) and (B), or may be the reminder subtracting the total ratio of the above-mentioned formulae (A) and (B) and the above-mentioned the fourth component, and, for example, it is 0 mol % to 90 mol %, preferably 3 mol % to 88 mol %, and further preferably 5 mol % to 87 mol %. In addition, the compound represented by the formula (C) may be two or more kinds.

The copolymer according to the present invention may be copolymerized with, as further optional fifth component, an ethylenically unsaturated monomer, or a polysaccharide or a derivative thereof. Examples of the ethylenically unsaturated monomer may be mentioned one kind or two or more kinds of the ethylenically unsaturated monomers selected from the group consisting of (meth)acrylic acid and an ester thereof; vinyl acetate; vinylpyrrolidone; ethylene; vinyl alcohol; and a hydrophilic functional derivative thereof. Examples of the polysaccharides or derivatives thereof may be mentioned a cellulose-based polymer such as hydroxyalkyl cellulose (for example, hydroxyethyl cellulose or hydroxypropyl cellulose), etc., starch, dextran and curdlan.

The hydrophilic functional derivative refers to an ethylenically unsaturated monomer having a hydrophilic functional group or structure. Examples of the hydrophilic functional group or structure may be mentioned a betaine structure; an amide structure; an alkylene glycol residue; an amino group; and a sulfinyl group, etc.

The betaine structure means a monovalent or a divalent group of a compound having an amphoteric center of a quaternary ammonium type cation structure and an acidic anion structure and may be mentioned, for example, a phosphorylcholine group:

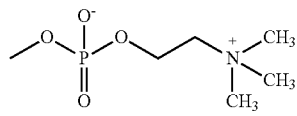

Examples of the ethylenically unsaturated monomer having such a structure may be mentioned 2-methacryloyloxyethylphosphorylcholine (MPC), etc.

The amide structure means a group represented by the following formula:

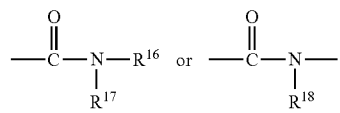

[here, $R^{16}$, $R^{17}$ and $R^{18}$ each independently represent a hydrogen atom or an organic group (for example, a methyl group, a hydroxymethyl group or a hydroxyethyl group, etc.)].

Examples of the ethylenically unsaturated monomer having such a structure may be mentioned (meth)acrylamide, N-(hydroxymethyl)(meth)acrylamide, etc. Further, the monomer or a polymer having such a structure is disclosed in, for example, JP 2010-169604A, etc.

The alkylene glycol residue means an alkyleneoxy group (-Alk-O—) which remains after a hydroxyl group(s) at one side terminal or both terminals of the alkylene glycol (HO-Alk-OH; here, Alk is an alkylene group having 1 to 10 carbon atoms) is/are subjected to condensation reaction with other compound(s), and a poly(alkyleneoxy) group in which alkyleneoxy units are repeated is also included. Examples of the ethylenically unsaturated monomer having such a structure may be mentioned 2-hydroxyethyl(meth)acrylate, methoxypolyethylene glycol (meth)acrylate, etc. Further, the monomer or the polymer having such a structure is disclosed in, for example, JP 2008-533489A, etc.

The amino group means a group represented by the formula: —$NH_2$, —$NHR^{19}$ or —$NR^{20}R^{21}$ [here, $R^{19}$, $R^{20}$ and $R^{21}$ each independently represent an organic group (for example, a linear or branched alkyl group having 1 to 5 carbon atoms, etc.)]. In the amino group of the present invention, a quaternized or chlorinated amino group is included. Examples of the ethylenically unsaturated monomer having such a structure may be mentioned dimethylaminoethyl (meth)acrylate, 2-(t-butylamino)ethyl (meth)acrylate, methacryloylcholine chloride, etc.

The sulfinyl group means a group represented by the following formula:

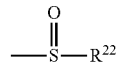

[here, $R^{22}$ is an organic group (for example, an organic group having 1 to 10 carbon atoms, preferably, an alkyl group having 1 to 10 carbon atoms which has one or more hydroxyl group, etc.)].

As a polymer having such a structure, there may be mentioned a copolymer disclosed in the publication of JP 2014-48278A, etc.

<Manufacturing Method of Copolymer>

The copolymer according to the present invention can be synthesized by the methods of radical polymerization, anion polymerization, cation polymerization, etc., which are general synthetic methods of an acrylic polymer or a methacrylic polymer, etc. The form can be taken various kinds of methods such as solution polymerization, suspension polymerization, emulsion polymerization, bulk polymerization, etc.

As the solvent for the reaction, it may be water, phosphate-buffered saline or an alcohol such as ethanol, etc., or a mixed solvent in which these are combined, and desirably contains water or ethanol. Further, it is preferable to contain 10% by mass or more and 100% by mass or less of water or ethanol. Moreover, it is preferable to contain 50% by mass or more and 100% by mass or less of water or ethanol. Furthermore, it is preferable to contain 80% by mass or more and 100% by mass or less of water or ethanol. Still further, it is preferable to contain 90% by mass or more and 100% by mass or less of water or ethanol. It is preferable that the sum of water and ethanol is 100% by mass.

As a reaction concentration, for example, a concentration of a monomer containing a group represented by the above-mentioned formula (a), a monomer containing a group represented by the above-mentioned formula (b), and in some cases, a monomer containing a group represented by the above-mentioned formula (c) in the reaction solvent is preferably made 0.01% by mass to 4% by mass. If the concentration exceeds 4% by mass, for example, the copolymer sometimes gelled in the reaction solvent due to strong association property possessed by the phosphate group represented by the formula (a). If the concentration is less than 0.01% by mass, a concentration of the obtained varnish is too low, so that it is difficult to prepare a composition for forming a coating film for obtaining a coating film with a sufficient film thickness. The concentration is more preferably 0.01% by mass to 3% by mass, for example, 3% by mass or 2% by mass.

In the synthesis of the copolymer according to the present invention, a monomer containing a group represented by the above-mentioned formula (a) and a monomer containing a group represented by the above-mentioned formula (b) are, for example, made a salt described in the formula (1), then, in some cases, a monomer containing a group represented by the above-mentioned formula (c) is added and polymerized to prepare a copolymer.

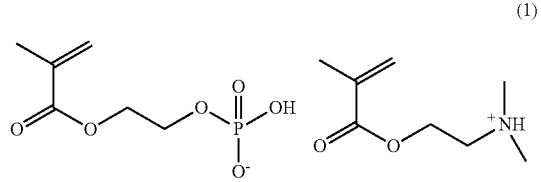

(1)

The phosphate group-containing monomer is a monomer easily associated, so that when it is to be added dropwise in the reaction system, it may be added dropwise in the reaction solvent little by little so as to rapidly disperse therein. Further, the reaction solvent may be heated (for example, 40° C. to 100° C.) so as to raise solubility of the monomer and the polymer.

In order to efficiently proceed the polymerization reaction, it is desirable to use a polymerization initiator. The polymerization initiator may be used 2,2'-azobis(isobutyronitrile), 2,2'-azobis(2-methylbutyronitrile), 2,2'-azobis(2,4-dimethyl-valeronitrile) (available from Wako Pure Chemical Industries, Ltd.; VA-065, 10 hour half-life temperature; 51° C.), 4,4'-azobis(4-cyanovaleric acid), 2,2'-azobis(4-methoxy-2,4-dimethylvaleronitrile), 1,1'-azobis(cyclohexane-1-carbonitrile), 1-[(1-cyano-1-methylethylazo]formamide, 2,2'-azobis[2-(2-imidazolin-2-yl)propane], 2,2'-azobis(2-methylpropionamidine) dihydrochloride, 2,2'-azobis[2-methyl-N-(2-hydroxyethyl)-propionamide] (available from Wako Pure Chemical Industries, Ltd.: VA-086, 10 hour half-life temperature; 86° C.), benzoyl peroxide (BPO), 2,2'-azobis[N-(2-carboxyethyl)-2-methylpropionamidine] n-hydrate (available from Wako Pure Chemical Industries, Ltd.: VA-057, 10 hour half-life temperature; 57° C.), 4,4'-azobis(4-cyanopentanoic acid) (available from Wako Pure Chemical Industries, Ltd.: V-501), 2,2'-azobis[2-(2-imidazolin-2-yl)propane] dihydrochloride (available from Wako Pure Chemical Industries, Ltd.: VA-044, 10 hour half-life temperature; 44° C.), 2,2'-azobis[2-(2-imidazolin-2-yl)propane] disulfate dihydrate (available from Wako Pure Chemical Industries, Ltd.: VA-046B, 10 hour half-life temperature; 46° C.), 2,2'-azobis[2-(2-imidazolin-2-yl)propane] (available from Wako Pure Chemical Industries, Ltd.: VA-061, 10 hour half-life temperature; 61° C.), 2,2'-azobis(2-amidinopropane) dihydrochloride (available from Wako Pure Chemical Industries, Ltd.: V-50, 10 hour half-life temperature; 56° C.), peroxydisulfuric acid or t-butylhydroperoxide, etc., and among these, ion balance and solubility in water are considered, it is desirable to use either of 2,2'-azobis[2-methyl-N-(2-hydroxyethyl)propionamide], 2,2'-azobis[N-(2-carboxyethyl)-2-methylpropionamidine] n-hydrate, 4,4'-azobis(4-cyanopentanoic acid), 2,2'-azobis[2-(2-imidazolin-2-yl)propane] dihydrochloride, 2,2'-azobis[2-(2-imidazolin-2-yl)propane] disulfate dihydrate, 2,2'-azobis[2-(2-imidazolin-2-yl)propane], 2,2'-azobis(2-amidinopropane) dihydrochloride or peroxydisulfuric acid.

As an amount of the polymerization initiator to be added, it is 0.05% by mass to 10% by mass based on the total mass of the monomer.

The reaction conditions are to carry out stirring in an oil bath, etc., as the reaction vessel heating to 50° C. to 200° C. for 1 hour to 48 hours, more preferably at 80° C. to 150° C. for 5 hours to 30 hours to proceed the polymerization reaction whereby a copolymer according to the present invention can be obtained. The reaction atmosphere is preferably a nitrogen atmosphere. As a reaction procedure, whole reaction substances may be charged in the reaction solvent at room temperature and then these may be heated to the above-mentioned temperature and polymerized, or all or a part of the mixture of the reaction substances may be added dropwise little by little into a previously heated solvent.

For example, as the latter reaction procedure, a mixture containing the compounds represented by the above-mentioned formulae (A), (B) and (C), a solvent and a polymerization initiator is added dropwise into a solvent maintained at a temperature higher than the 10 hour half-life temperature of the polymerization initiator to carry out the reaction (polymerization). By employing such a reaction procedure and temperature condition, a concentration of the compound represented by the above-mentioned formula (A), formula (B) or the formula (C) in the reaction solvent can be made, for example, 0.01% by mass to 10% by mass. In this case, even if the concentration exceeds 4% by mass, the dropping phase and the reaction phase become transparent and uniform solution before the reaction, and gelation of the copolymer in the reaction solvent after the reaction can be suppressed.

The molecular weight of the copolymer according to the present invention may be about several thousand to several million, and preferably 5,000 to 5,000,000. It is further preferably 10,000 to 2,000,000. In addition, it may be either of a random copolymer, a block copolymer or a graft copolymer, there is no particular limitation on the copolymerization reaction itself for manufacturing the copolymer, and a conventionally known method synthesizing in a liquid can be used such as polymerization utilizing radical polymerization, ionic polymerization, photopolymerization, emulsion polymerization, etc. These can be used any of the copolymers of the present invention solely or a plurality of the copolymers are mixed and the ratio thereof may be changed depending on the objective uses.

The various kinds of the copolymers thus manufactured may be a two-dimensional polymer or a three-dimensional polymer, and are in a state dispersed in a solution containing water. That is, in the varnish containing these polymers, it is not preferable to cause ununiform gelation or turbid precipitation, but preferable to be a transparent varnish, a varnish in a dispersed colloidal state, or a sol.

The cell culture container of the present invention is characterized in that the above-mentioned copolymer is coated onto at least a part of the surface of the container, preferably coated onto an inside surface of the container which is bringing into contact with cells and a culture solution, and more preferably coated onto the whole surface of the container. Coating of the above-mentioned copolymer onto the cell culture container can be formed by a conventionally known means, specifically by the means mentioned at the column of <<Manufacturing method of cell culture container>> and Examples hereinbelow. A thickness of the coating of the cell culture container of the present invention is optionally selected depending on a shape or purpose of the container, preferably 10 to 1,000 Å, more preferably 10 to 500 Å, and particularly preferably 10 to 300 Å. The cell culture container of the present invention has an excellent function of inhibiting adhesion of cells and proteins by such a coating.

<<Manufacturing Method of Cell Culture Container>>

A second embodiment of the present invention is directed to a method for manufacturing a cell culture container which comprises a step of bringing a coating agent into contact with a surface of a cell culture container having at least one opened minute space which has a volume of 20 µL or less, to form a coating film having a difference between the maximum film thickness and the minimum film thickness of 1,000 Å or less onto at least a part of the surface portion of the container constituting the minute space, wherein the coating agent contains a copolymer having a recurring unit which contains a group represented by the following formula (a), a recurring unit which contains a group represented by the following formula (b), and preferably a recurring unit which contains a group represented by the following formula (c):

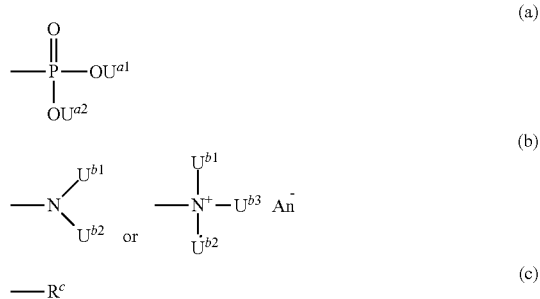

(wherein, $U^{a1}$, $U^{a2}$, $U^{b1}$, $U^{b2}$ and $U^{b3}$, $R^c$ and $An^-$ have the same meanings as defined above).

<Coating Step>

In the coating step of the manufacturing method of the cell culture container of the present invention, the copolymer is coated onto at least a part of the surface portion of the container that constitutes a minute space having a volume of 20 µL or less and opened at the surface of the container. For example, when the container is a round-bottom multi-well plate, only the portion of depression of the well may be coated, but whole plate may be coated. Here, the container and the copolymer are as described in the above-mentioned items <Container> and <Copolymer>, respectively.

The coating step is not particularly limited, and may be carried out by any of the coating means (for example, coating, dipping, etc.) known to those skilled in the art which can contact the container and the coating agent containing the copolymer. For example, it can be carried out by coating a varnish containing a copolymer as a coating agent onto the container, or by dipping the container in a varnish containing a copolymer as a coating agent. It is preferably carried out by dipping the container in a varnish containing a copolymer.

The varnish containing the copolymer may be prepared by dissolving the copolymer obtained in the above-mentioned item <Manufacturing method of copolymer> in a suitable solvent with a desired concentration, or a reaction solution containing the copolymer obtained by such a manufacturing method may be used as a varnish as such or after diluting a desired solid content concentration. As the solvent contained in the varnish, water, phosphate-buffered saline (PBS) and an alcohol are mentioned. As the alcohol, there may be mentioned an alcohol having 2 to 6 carbon atoms, for example, ethanol, propanol, isopropanol, 1-butanol, 2-butanol, isobutanol, t-butanol, 1-pentanol, 2-pentanol, 3-pentanol, 1-heptanol, 2-heptanol, 2,2-dimethyl-1-propanol (=neopentyl alcohol), 2-methyl-1-propanol, 2-methyl-1-butanol, 2-methyl-2-butanol (=t-amyl alcohol), 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol and cyclohexanol, which may be used alone or a mixed solvent of a combination thereof, and it is preferably selected from water, PBS and ethanol. For dissolution of the copolymer, water is necessarily contained.

A concentration of the copolymer in the varnish is 0.01 to 4% by mass, further desirably 0.01 to 3% by mass, further desirably 0.01 to 2% by mass, and further desirably 0.01 to 1% by mass. If the concentration of the copolymer is less than 0.01% by mass, a coating which a sufficient film thickness cannot be formed, while if it exceeds 4% by mass, storage stability of the varnish becomes worse, and there is a possibility to cause precipitation of the dissolved material or gelation.

Incidentally, to the varnish, in addition to the above-mentioned copolymer and the solvent, other substances may be added within the range that does not impair the properties of the obtainable coating, if necessary. As the other substances, there may be mentioned preservatives, surfactants, primers that enhance adhesive property with the substrate (container), fungicides and sugars, etc.

In order to adjust ion balance of the copolymer in the varnish, a pH of the varnish containing the copolymer may be adjusted in advance. Adjustment of the pH may be carried out, for example, by adding a pH adjusting agent to the varnish containing the copolymer and made the pH of the varnish 3.5 to 8.5, preferably 4.0 to 8.0. A kind of the usable pH adjusting agent and an amount thereof can be optionally selected depending on the concentration of the copolymer in the varnish or an existing ratio of the anion and the cation in the copolymer, and the like. Examples of the pH adjusting agent may be mentioned organic amines such as ammonia, diethanolamine, pyridine, N-methyl-D-glucamine, tris(hydroxymethyl)aminomethane, etc.; alkali metal hydroxides such as potassium hydroxide, sodium hydroxide, etc.; alkali metal halides such as potassium chloride, sodium chloride, etc.; inorganic acid such as sulfuric acid, phosphoric acid, hydrochloric acid, carbonic acid, etc., or alkali metal salts thereof; quaternary ammonium cation such as choline, etc.; or a mixture thereof (for example, a buffer such as phosphate buffered saline, etc.). Among these, ammonia, diethanolamine, N-methyl-D-glucamine, tris(hydroxymethyl)aminomethane, sodium hydroxide and choline are preferable, and in particular, ammonia, diethanolamine, sodium hydroxide and choline are preferable.

Such a varnish containing such the copolymer is contacted with the container to form a coating onto at least a part of the surface thereof. The coating is preferably formed onto whole surface portion of the container constituting the minute space, and more preferably formed onto whole part of the cell culture container.

Incidentally, before the coating step, the surface of the container may be washed by applying it to a conventionally known UV/ozone treatment. Such a washing step can be carried out by using a commercially available UV/ozone cleaner, etc.

<Drying, Washing and Sterilization Step>

After the coating step, the coated container is preferably dried at a temperature of −200° C. to 200° C. By drying, the solvent in the above-mentioned composition for forming the coating film is removed and also the formula (a) and the formula (b) of the copolymer according to the present invention form ionic bonds to completely adhere to the substrate. A film thickness of the coating of the cell culture container of the present invention is preferably 10 to 1,000 Å, more preferably 10 to 500 Å, and particularly preferably 10 to 300 Å. The present inventors have found that in the manufacturing method of the cell culture container of the present invention, it does not require a treatment at a high temperature, a coating having desired characteristics is formed onto the surface of the container by a treatment at a low temperature, and has excellent durability and an excellent function of inhibiting adhesion of cells and proteins in spite of thin film thickness of several tens to several hundreds Å.

Drying can be carried out, for example, at room temperature (10° C. to 35° C., for example, 25° C.), and may be carried out, for example, 40° C. to 50° C. to form a coating film more rapidly. In addition, it may be carried out at an extremely low temperature to a low temperature (around −200° C. to −30° C.) by the freeze drying method. The freeze drying is called as vacuum freeze-drying, and is a method in which a material to be desired to dry is cooled with a refrigerant in general and remove the solvent under a vacuum state by sublimation. A general refrigerant to be used in the freeze drying may be mentioned a mixed medium of dry ice and methanol (−78° C.), liquid nitrogen (−196° C.), etc. A more preferable drying temperature is 10° C. to 180° C., and a further preferable drying temperature is 25° C. to 150° C.

Incidentally, before and/or after the drying step, the surface of the coated container may be washed with an alcohol having 1 to 5 carbon atoms such as ethanol, etc., and/or water. Such a washing step may be carried out at a temperature of 0° C. to 60° C., preferably 25° C. (room temperature) to 40° C. for 30 minutes to 48 hours, preferably for 1 to 24 hours.

Further, after the drying step, in order to remove impurities, unreacted monomer, etc., remained in the coating, and further, to adjust ion balance of the copolymer in the film, it may be washed by running water washing or ultrasonic wave washing, etc., using at least one kind of a solvent selected from the group consisting of water and an aqueous solution containing an electrolyte. Here, water or the aqueous solution containing an electrolyte may be a material heated, for example, in the range of 40° C. to 95° C. The aqueous solution containing an electrolyte is preferably PBS and physiological saline (containing only sodium chloride), Dulbecco's phosphate buffered saline, Tris buffered physiological saline, HEPES buffered physiological saline and veronal buffered physiological saline, and particularly preferably PBS.

The coating formed onto the surface of the container does not elute and remains firmly adhered to the substrate (i.e., the container) even when it is washed with alcohol, water, and PBS, etc. The formed coating has a function of inhibiting adhesion of various biological substances including cells and proteins. Accordingly, the cell culture container of the present invention is a material, in addition to inhibit adhesion of cells and proteins, excellent in durability to the solvent.

If necessary, in order to sterilize the coated container, a conventionally known sterilization treatment such as radiation, electron beam, ethylene oxide, autoclave, etc., may be carried out.

<<Producing Method of Cell Aggregates>>

A third embodiment of the present invention is a method of producing cell aggregates which comprises using the cell culture container of the present invention and the cell culture container obtained by the manufacturing method of the present invention (hereinafter, both are referred to as the "cell culture container of the present invention"). When the cell culture container of the present invention is used, adhesion of the cell aggregates to the surface of the container is suppressed, and elution of the coating to the culture solution is suppressed, so that cell aggregates can be cultured in a state without any stimulation from the container. The cell aggregates are preferably cultured by using a medium which comprises containing a polysaccharide (in particular, deacylated gellan gum) having an effect of floating cells or tissues in the cell culture container of the present invention. Specific composition and culture method of such a medium are disclosed in, for example, WO 2014/017513.

(Evaluation of Contact Angle)

One aspect of the evaluation method of the contact angle is mentioned the following method.

[Evaluation of Static Contact Angle Meter]

The various kinds of substrates onto which the coating film is formed are evaluated using a fully automatic contact angle meter (Kyowa Interface Science Co., Ltd., DM-701). An evaluation temperature is, for example, at 25° C. (in the air and in water). The static contact angle is carried out evaluations both of the contact angle in water in which the contact angle measurement of bubbles is carried out by installing various substrates upside down in water, in addition to the contact angle measurement of water droplets in the air.

EXAMPLES

In the following, the present invention is explained in more detail based on Synthetic Examples, Examples, Test Examples, etc., but the present invention is not limited by these.

A weight average molecular weight of the copolymer shown in the following Synthetic Examples is a measurement result by Gel Filtration Chromatography (hereinafter abbreviated to as GFC), or Gel Permeation Chromatography (hereinafter abbreviated to as GPC). Measurement conditions, etc., are as follows.

(GFC Measurement Conditions)
Apparatus: Prominence (manufactured by Shimadzu Corporation)
GFC column: TSKgel GMPWXL (7.8 mm I.D.×30 cm)×2 to 3
Flow rate: 1.0 mL/min
Eluent: Ionic substance-containing aqueous solution, or mixed solution of EtOH
Column temperature: 40° C.
Detector: RI
Injection concentration: polymer solid content of 0.05 to 0.5% by mass
Injection amount: 100 µL
Calibration curve: Cubic approximation curve
Standard samples: polyethylene oxide (available from Agilent Technologies)×10 kinds Synthetic Example 1

To 7.97 g of ethanol and 23.92 g of pure water was added 5.00 g of acid phosphoxyethyl methacrylate (product name; Phosmer M, available from UniChemical Co, non-volatile content by evaporation to dryness method at 100° C. for 1 hour: 91.8%, a mixture of acid phosphoxyethyl methacrylate (44.2% by mass), bis[2-(methacryloyloxy)ethyl] phosphate (28.6% by mass) and other substance(s) (27.2% by mass)) and the mixture was stirred and dissolved, then, while maintaining to 20° C. or lower, 3.82 g of 2-(dimethylamino) ethyl methacrylate (available from Tokyo Chemical Industry Co., Ltd.) and 0.04 g of 2,2'-azobis(N-(2-carboxyethyl)-2-methylpropionamidine) n-hydrate (product name; VA-057, available from Wako Pure Chemical Industries, Ltd.) were successively added while maintaining to 20° C. or lower. A mixed liquid in which all of the above-mentioned components were charged which became uniform by sufficient stirring was introduced into a dropping funnel. On the other hand, 47.84 g of pure water was separately charged in a three-necked flask attached with a cooling tube, and this was nitrogen-flowed and heated to the reflux temperature while stirring. While maintaining this state, the dropping funnel into which the above-mentioned mixed liquid had been introduced was set to the three-necked flask, and the mixed liquid was added dropwise into the boiling liquid over 1 hour. After dropping, the mixture was heated and stirred for 24 hours in the state of maintaining the above-mentioned circumstance to obtain 88.60 g of a varnish containing a copolymer with a solid content of about 9.70% by mass. A weight average molecular weight of the obtained transparent liquid by GFC was about 280,000.

Preparation Example 1

To 5.00 g of the varnish containing the copolymer obtained in the above-mentioned Synthetic Example 1 were added 56.39 g of pure water, 28.50 g of ethanol and 0.85 g of 1 mol/L sodium hydroxide aqueous solution (1N) (available from KANTO CHEMICAL CO., INC.) and the mixture was sufficiently stirred to prepare a coating agent. A pH thereof was 7.5. The obtained coating agent was spin coated to the silicon wafer mentioned below with 1,500 rpm for 60 seconds, and dried in an oven at 50° C. for 24 hours. Thereafter, washing was sufficiently carried out with PBS and pure water to obtain a silicon wafer onto which a coating film had been formed. When the film thickness of the coating film of the silicon wafer was confirmed by an optical type interference thickness meter, then it was 55 Å.

Preparation Example 2

To 29.98 g of ethanol and 2 g of pure water was dissolved 1.2 g of poly(2-hydoxyethyl methacrylate) (available from Sigma Aldrich Japan K.K.) and the mixture was sufficiently stirred to prepare a coating agent. The obtained coating agent was spin coated to the silicon wafer similar to Preparation Example 1, and dried in an oven at 50° C. for 24 hours. Thereafter, washing was sufficiently carried out with pure water to obtain a coating film on a silicon wafer or plate. When the film thickness of the coating film of the silicon wafer was confirmed by an ellipsometer, then it was 1,960 Å.

Example 1 and Comparative Example 1: Preparation of Coating Plate (Polystyrene)

To Corning #3893 (1,536 well, volume 12.5 µL/well, cell adhesion treatment and gamma ray sterilization treatment had carried out, material: polystyrene) and Greiner #782180 (1,536 well, volume 12.6 µL/well, cell adhesion treatment and gamma ray sterilization treatment had carried out, material: polystyrene), 3 µL of the coating agent of Preparation Example 1 was injected into separate wells. These were allowed to stand for 1 hour and then they were removed and dried in an oven at 50° C. for 24 hours. Thereafter, the coated well was washed with 10 µL of pure water each three times to obtain a coating plate of Example 1. Similarly, 3 µL of the coating agent of Preparation Example 2 was injected into separate wells of Corning #3893 and Greiner #782180, and dried in an oven at 50° C. for 24 hours to obtain a coating plate of Comparative example 1. These plates were used in the following Test Example 1. As a negative control, a well which had not been applied a coating was used.

Test Example 1: Cell Adhesion Inhibiting Effect (Preparation of Cells)
As the cells, mouse embryonic fibroblasts C3H/10T1/2 (available from DS Pharma Biomedical Co., Ltd.) were used. The medium used for culture of the cells was a basal medium eagle (BME) (available from Thermo Fisher Scientific Co., Ltd.) containing 10% FBS (available from HyClone) and an L-glutamine-penicillin-streptomycin stabilizing solution (available from Sigma-Aldrich Corporation). The cells were statically cultured for 2 days or more using a petri dish (schale) (10 mL of medium) having a diameter of 10 cm while in a state of maintaining a 5% carbon dioxide concentration in a 37° C./$CO_2$ incubator. Subsequently, the present cells were washed with 5 mL of PBS, then, 1 mL of trypsin-EDTA solution (available from Invitrogen) was added and the cells were detached, and suspended in 10 mL of the above-mentioned medium, respectively. This suspension was centrifuged (manufactured by Tommy Seiko Co., Ltd., model number LC-200, 1,000 rpm/3 minutes, room temperature), then the supernatant was removed and the above-mentioned medium was added to prepare a cell suspension.

(Cell Adhesion Test)
To each plate prepared in the above-mentioned Example 1 and Comparative example 1, and to a plate to which the coating of the present invention was not applied as a negative control, 5 µL of each cell suspension was added so as to be 100 cells/well. Thereafter, the samples were allowed to stand in a $CO_2$ incubator at 37° C. for 4 days in the state of maintaining a 5% carbon dioxide concentration.
(Observation of Cell Adhesion and Plate Coatability)

One day after culture, adhesion of the cells to the plate of Example 1, the plate of Comparative example 1 and the plate of negative control were compared based on observation (magnification: 4-fold) with an inverted microscope (manufactured by Olympus Corporation, CKX31). The results of each plate (1 day after culture) are shown in FIG. 1 to FIG. 6. With regard to coatability and cell adhesion of the film, and presence or absence of bubbles after addition to the medium, the results are shown in Table 1.

With regard to cell adhesion inhibition, the case where the cells were adhered was indicated as X, and the case where the cells were not adhered was indicated as ◯. With regard to bubble biting, after adding the medium to the wells, the case where no bubble was observed was indicated as ◯, and the case where bubbles were observed was indicated as X. With regard to coatability, the case where an image derived from the coating material confirmed in the observation region other than the cells and bubbles was confirmed was judged as coating failure and indicated as X, and the case where the same image as the negative control was maintained was indicated as ◯.

TABLE 1

| | 1536 well plate (available from Corning) | | | 1536 well plate (available from Greiner) | | |
|---|---|---|---|---|---|---|
| | Cell adhesion inhibition | Bubble biting | Coatability | Cell adhesion inhibition | Bubble biting | Coatability |
| Negative control | X | ◯ | — | X | ◯ | — |
| Example 1 | ◯ | ◯ | ◯ | ◯ | ◯ | ◯ |
| Comparative Example 1 | ◯ | X | X | ◯ | ◯ | X |

In the plate of negative control, the cells were adhered but no bubble biting was observed. In the plate of Comparative example 1, adhesion of the cells was not observed, but bubble biting and coating failure were observed. Good coatability was confirmed only in Example 1, and neither adhesion of the cells nor bubble biting was observed.

Example 2 and Comparative Example 2:
Preparation of Coating Plate (PDMS)

(Preparation of PDMS Coating Plate)

Figure 7:
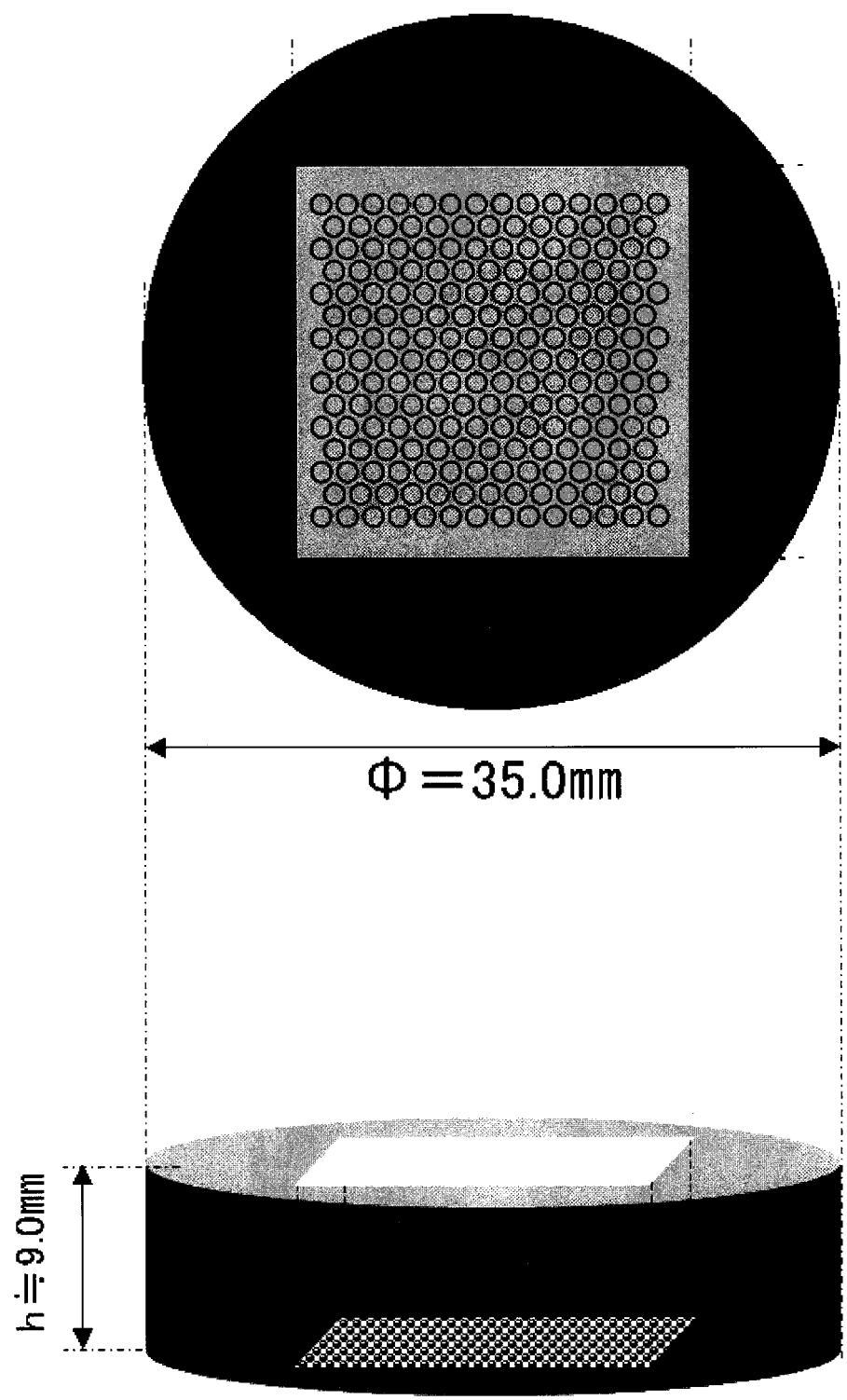
FIG. 7 is an explanation drawing (1) for preparation of a PDMS coating plate.
Figure 8:
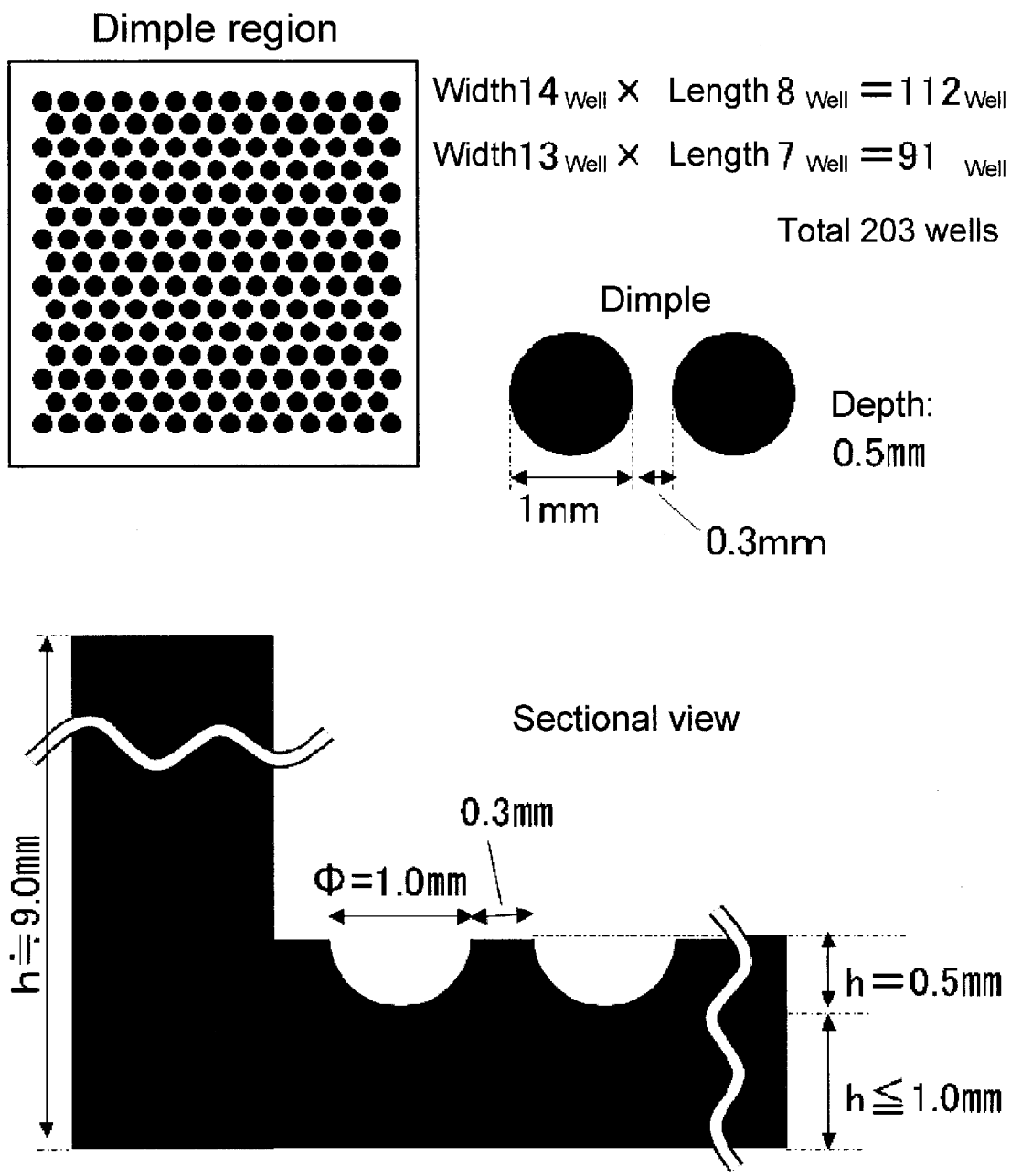
FIG. 8 is an explanation drawing (2) for preparation of a PDMS coating plate.
Figure 9:
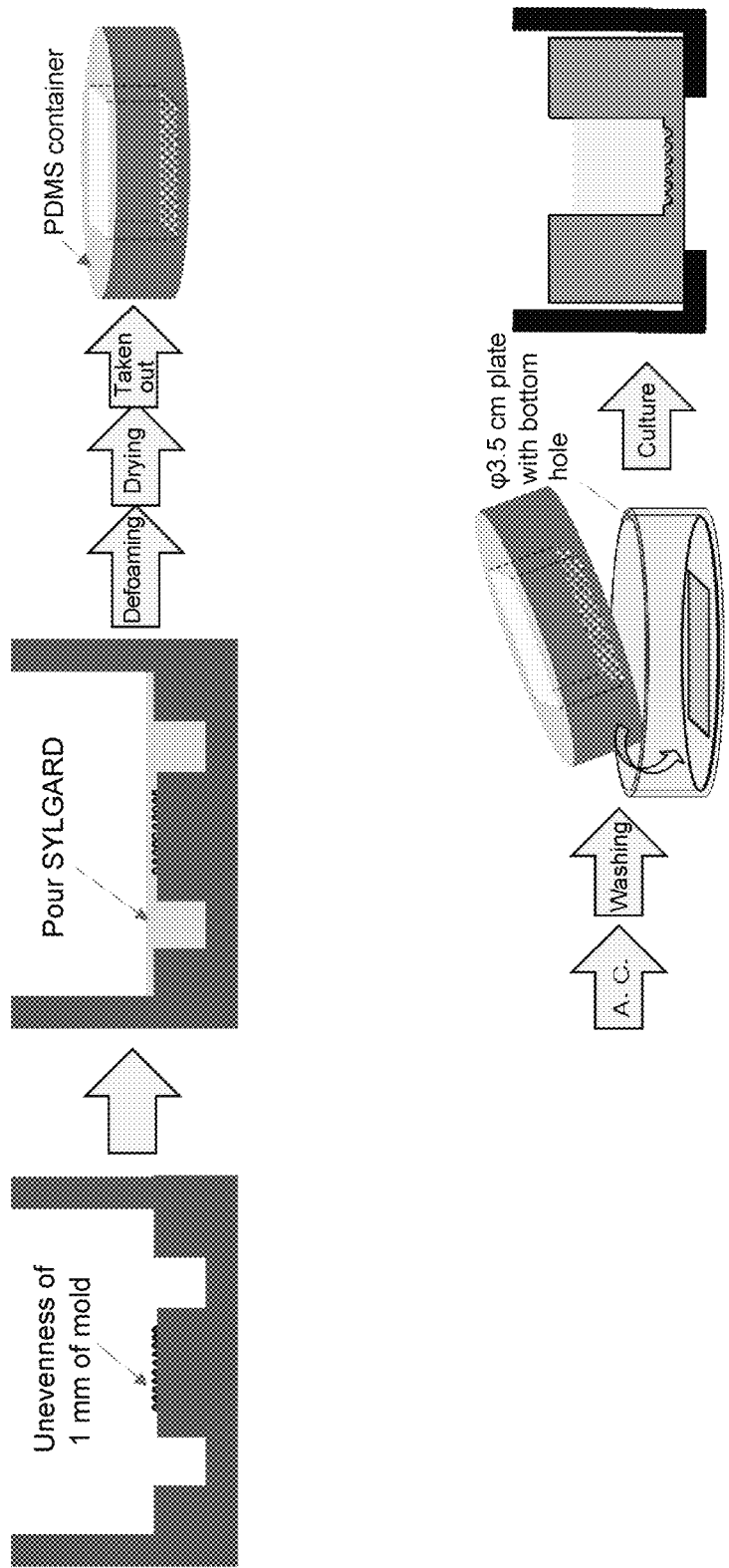
FIG. 9 is an explanation drawing (3) for preparation of a PDMS coating plate.
Figure 10:
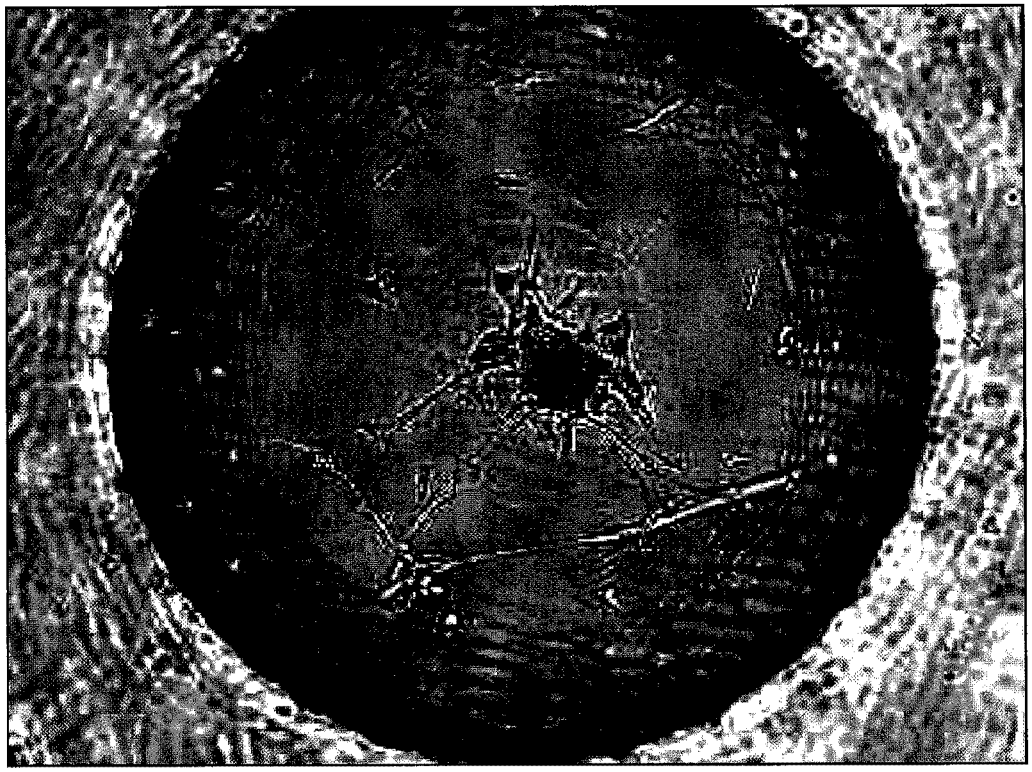
FIG. 10 is a photograph of observation results of negative control in (Table 2) by an inverted microscope.

A mold which can transfer the shape of FIG. 7 is prepared. With a ratio of 10.00 g of a main agent of SYLGARD 184 silicone elastomer (available from Dow Corning) and 1.00 g of a curing agent, these are mixed, stirred and poured into the prepared mold. After defoaming with a vacuum pump, it is dried in an oven at 80° C. for 1 hour. After cooling to room temperature, a cured product of PDMS is taken out from the mold. The cured product is immersed in pure water, and an autoclave sterilization treatment is carried out at 120° C. for 60 minutes. The bottom of ASNOL schale (petri dish): φ40×13.5 mm (manufactured by AS ONE Corporation) is cut in comply with the dimple region in FIG. 8 with 20 mm square, and the PDMS cured product is washed with 70% ethanol, and then placed in the petri dish and capped. It is made a PDMS coating plate having a dimple number of 203, where a diameter of 1 mm (a distance between dimples of 0.3 mm), a depth of 0.5 mm, a volume per one dimple of about 0.3 μL (see FIG. 9).
(Preparation of PDMS Coating Plate)

Into separate plates of the PDMS coating plates prepared as mentioned above was injected each 2 mL of the coating agent of Preparation Example 1. These were allowed to stand for 1 hour, the coating agent was removed and the plates were dried in an oven at 50° C. for 24 hours. Thereafter, the coated plates were washed with 2 mL of pure water each with three times to obtain coating plates of Example 2. Similarly, into separate plates of the PDMS coating plate prepared as mentioned above was injected each 2 mL of the coating agent of Preparation Example 2, and the plates were dried in an oven at 50° C. for 24 hours to obtain coating plates of Comparative example 2. These plates were used in the following Test Example 2. As a negative control, a plate not applied the coating was used.

Test Example 2: Cell Adhesion Inhibiting Effect (Preparation of Cells)

As the cells, normal human dermal fibroblast, juvenile foreskin NHDF (available from KURABO INDUSTRIES, LTD.) were used. The medium used for culture of the cells was a D-MEM low glucose medium (available from Wako Pure Chemical Industries, Ltd.) containing 10% FBS (available from Gibco) and penicillin-streptomycin solution (available from Gibco).

The cells were statically cultured for 2 days or more using a petri dish (schale) (10 mL of medium) having a diameter of 10 cm while in a state of maintaining a 5% carbon dioxide concentration in a 37° C./$CO_2$ incubator. Subsequently, the present cells were washed with 5 mL of PBS, then, 1 mL of trypsin-EDTA solution (available from Wako Pure Chemical Industries, Ltd.) was added and the cells were detached, and suspended in 10 mL of the above-mentioned medium, respectively. This suspension was centrifuged (manufactured by Tommy Seiko Co., Ltd., model number LC-200, 1,270 rpm/3 minutes, room temperature), then the supernatant was removed and the above-mentioned medium was added to prepare a cell suspension.
(Cell Adhesion Test)

To each plate prepared in the above-mentioned Example 2 and Comparative example 2, and to a plate to which the coating of the present invention was not applied as a negative control, 2 mL of each cell suspension was added so as to be 30×10$^4$ cells/well. Thereafter, the samples were allowed to stand in a $CO_2$ incubator at 37° C. for 3 days in the state of maintaining a 5% carbon dioxide concentration.
(Observation of Cell Adhesion and Plate Coatability)

One day after culture, adhesion of the cells to the plate of Example 2, the plate of Comparative example 2 and the plate of negative control were compared based on observation (magnification: 4-fold and 10-fold) with an inverted microscope (manufactured by Nikon Corporation, ECLIPSE TS100). The results of each plate (1 day after culture) are shown in FIG. 10 to FIG. 13. With regard to coatability and cell adhesion of the film, and presence or absence of bubbles after addition to the medium, the results are shown in Table 2.

With regard to cell adhesion inhibition, the case where the cells were adhered or no spheroid was formed was indicated as X, and the case where the cells were not adhered and spheroids with nearly a circular shape were formed was indicated as ◯. With regard to bubble biting, after adding the medium to the wells, the case where no bubble was observed was indicated as ○, and the case where bubbles were observed was indicated as X. With regard to coatability, the case where an image derived from the coating material confirmed in the observation region other than the cells and bubbles was confirmed was judged as coating failure and indicated as X, and the case where the same image as the negative control was maintained was indicated as ○.

TABLE 2

|  | PDMS container | | |
| --- | --- | --- | --- |
|  | Cell adhesion inhibition Spheroids formation | Bubble biting | Coatability |
| Negative control | × | ○ | — |
| Example 2 | ○ | ○ | ○ |
| Comparative Example 2 | ○ | × | × |

Figure 11:
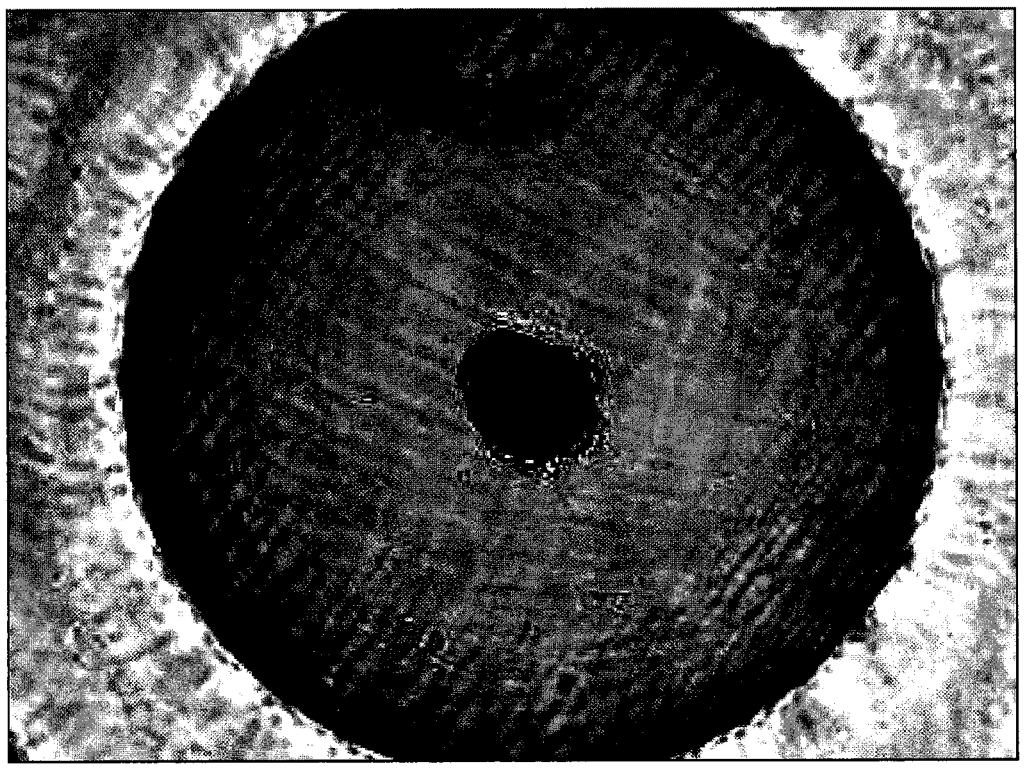
FIG. 11 is a photograph of observation results of Example 2 in (Table 2) by an inverted microscope.
Figure 12:
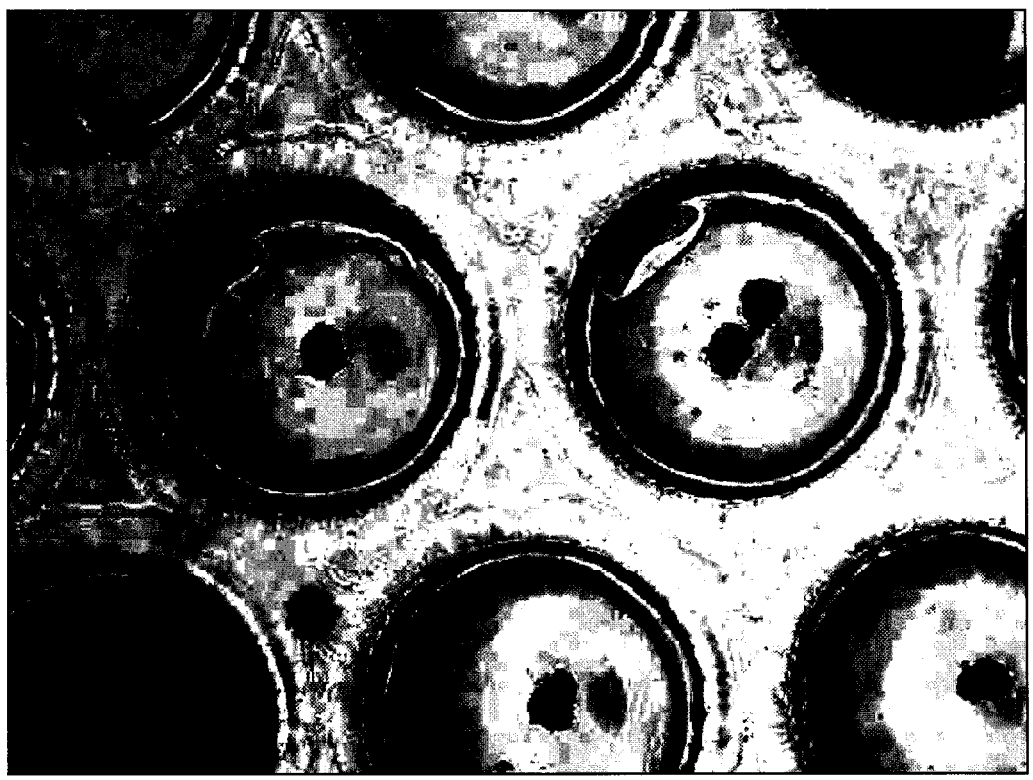
FIG. 12 is a photograph of observation results of Comparative example 2 in (Table 2) by an inverted microscope.
Figure 13:
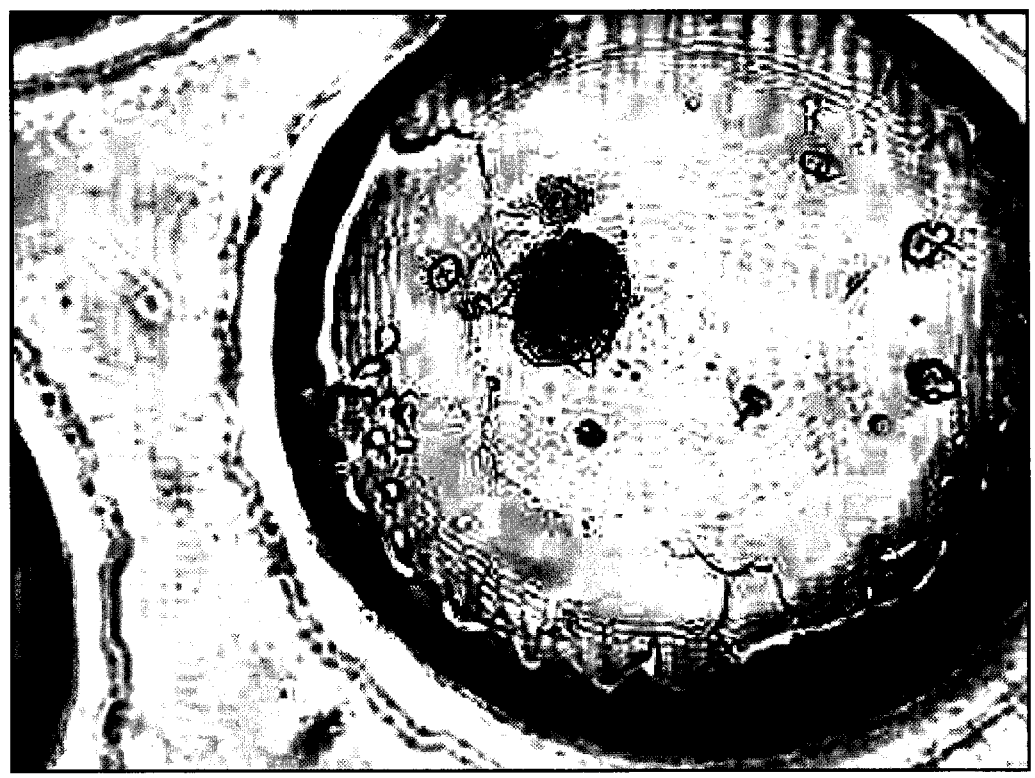
FIG. 13 is a photograph of observation results of Comparative example 2 in (Table 2) by an inverted microscope.

In the plate of negative control, the cells were adhered but no bubble biting was observed (see [FIG. 11]). In Example 2, good coatability was confirmed, no adhesion of the cells and good spheroids were observed, and no bubble biting was observed (see [FIG. 12]). Further, in Comparative example 2, spheroids were formed in a part of the wells but in a part of the wells, bubble biting was generated, further, coatability to the well was poor and peeling from the substrate was confirmed (see [FIG. 13] and [FIG. 14]).

UTILIZABILITY IN INDUSTRY

The cell culture container of the present invention is coated onto at least a part of the surface is coated by a copolymer having a specific group. Such a coating inhibits adhesion of the cells and the proteins to the surface of the container and the coating can firmly adhere to the surface of the container, so that elution of the coating into the culture solution is improved. Accordingly, the cell culture container of the present invention is advantageous in the point that cell aggregates can be cultured in a state free from any stimulation from the container.

Furthermore, even in a cell culture container having a minute space, a thin film coating can be formed uniformly without any defects such as bubble biting, etc., so that a cell culture container in which the quality is stabilized can be manufactured.

The invention claimed is:

1. A cell culture container comprising at least one opened minute space with a volume of 20 μL or less at a surface of the container, and a hydrophilic coating film containing a copolymer having the recurring units represented by formulae (a1) and (b1):

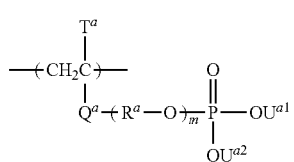

(a1)

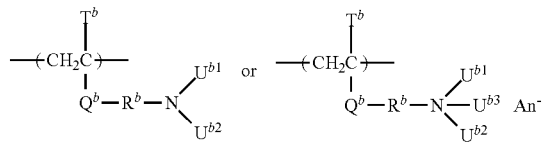

(b1)

wherein $T^a$, $T^b$, $U^{a1}$, $U^{a2}$, $U^{b1}$, $U^{b2}$ and $U^{b3}$ each independently represent a hydrogen atom or a linear or branched alkyl group having 1 to 5 carbon atoms, $Q^a$ and $Q^b$ represent an ester bond, $R^a$ and $R^b$ each independently represent a linear or branched alkylene group having 1 to 18 carbon atoms which may be substituted by halogen atom(s), $An^-$ represents an anion selected from the group consisting of a halide ion, an inorganic acid ion, a hydroxide ion and an isothiocyanate ion, and m represents an integer of 0 to 6, on the surface portion of the container constituting the minute space, wherein the hydrophilic coating film has no bubble therein and has a surface with a water contact angle in air of 0° to 120° and a bubble contact angle in water of 80° to 180°, and wherein the hydrophilic coating film is obtained by coating a varnish containing (i) the copolymer with a solid content of 0.01 to 4% by mass and (ii) water as a solvent.

2. The cell culture container according to claim 1, wherein the copolymer further has a recurring unit represented by formula (c1):

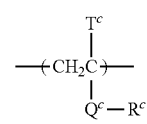

(c1)

wherein $T^c$ represents a hydrogen atom or a linear or branched alkyl group having 1 to 5 carbon atoms, $Q^c$ represent an ester bond, and $R^c$ represents a linear or branched alkyl group having 1 to 18 carbon atoms, a cyclic hydrocarbon group having 3 to 10 carbon atoms, an aryl group having 6 to 10 carbon atoms, an aralkyl group having 7 to 15 carbon atoms or an aryloxyalkyl group having 7 to 15 carbon atoms, where the above-mentioned aryl portion may be substituted by a linear or branched alkyl group having 1 to 5 carbon atoms which may be substituted by a halogen atom(s).

3. The cell culture container according to claim 2, wherein a difference between the maximum film thickness and the minimum film thickness of the hydrophilic coating film is 1,000 Å or less.

4. The cell culture container according to claim 3, wherein transmittance in a visible light region is 90% or more.

5. The cell culture container according to claim 4, wherein a material thereof is glass, a metal containing compound, a semi-metal containing compound or a resin.

6. The cell culture container according to claim 5, which is for the manufacture of cell aggregates.

7. The cell culture container according to claim 4, which is for the manufacture of cell aggregates.

8. The cell culture container according to claim 3, wherein a material thereof is glass, a metal containing compound, a semi-metal containing compound or a resin.

9. The cell culture container according to claim 3, which is for the manufacture of cell aggregates.

10. The cell culture container according to claim 2, wherein transmittance in a visible light region is 90% or more.

11. The cell culture container according to claim 2, wherein a material thereof is glass, a metal containing compound, a semi-metal containing compound or a resin.

12. The cell culture container according to claim 2, which is for the manufacture of cell aggregates.

13. The cell culture container according to claim 1, wherein a difference between the maximum film thickness and the minimum film thickness of the hydrophilic coating film is 1,000 Å or less.

14. The cell culture container according to claim 1, which is for the manufacture of cell aggregates.

15. The cell culture container according to claim 1, wherein transmittance in a visible light region is 90% or more.

16. The cell culture container according to claim 1, wherein a material thereof is glass, a metal containing compound, a semi-metal containing compound or a resin.

17. The cell culture container according to claim 1, wherein the hydrophilic coating film has no bubble therein upon addition of a medium to the cell culture container.

18. A method for manufacturing a cell culture container which comprises a step of bringing a coating agent into contact with a surface of a cell culture container having at least one opened minute space which has a volume of 20 μL or less, to form a hydrophilic coating film having a difference between the maximum film thickness and the minimum film thickness of 1,000 Å or less onto the surface portion of the container constituting the minute space, wherein the coating agent contains a copolymer having the recurring units represented by formulae (a1) and (b1):

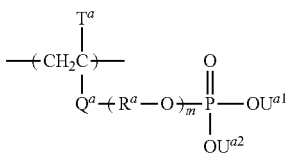

(a1)

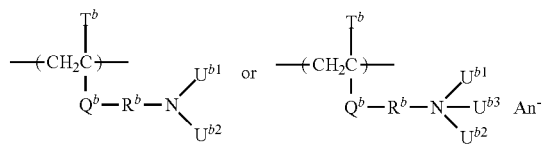

(b1)

wherein $T^a$, $T^b$, $U^{a1}$, $U^{a2}$, $U^{b1}$, $U^{b2}$ and $U^{b3}$ each independently represent a hydrogen atom or a linear or branched alkyl group having 1 to 5 carbon atoms, $Q^a$ and $Q^b$ represent an ester bond, $R^a$ and $R^b$ each independently represent a linear or branched alkylene group having 1 to 18 carbon atoms which may be substituted by halogen atom(s), An⁻ represents an anion selected from the group consisting of a halide ion, an inorganic acid ion, a hydroxide ion and an isothiocyanate ion, and m represents an integer of 0 to 6, wherein the coating agent contains (i) the copolymer with a solid content of 0.01 to 4% by mass and (ii) water as a solvent, and wherein the hydrophilic coating film has no bubble therein and has a surface with a water contact angle in air of 0° to 120° and a bubble contact angle in water of 80° to 180°.

19. The method for manufacturing a cell culture container according to claim 18, wherein the copolymer further has a recurring unit represented by the following formula (c1):

(c1)

wherein $T^c$ represents a hydrogen atom or a linear or branched alkyl group having 1 to 5 carbon atoms, $Q^c$ represent an ester bond, and $R^c$ represents a linear or branched alkyl group having 1 to 18 carbon atoms, a cyclic hydrocarbon group having 3 to 10 carbon atoms, an aryl group having 6 to 10 carbon atoms, an aralkyl group having 7 to 15 carbon atoms or an aryloxyalkyl group having 7 to 15 carbon atoms, where the aryl portion may be substituted by a linear or branched alkyl group having 1 to 5 carbon atoms which may be substituted by a halogen atom(s).

* * * * *